(12) United States Patent
Rzasa et al.

(10) Patent No.: US 10,773,094 B1
(45) Date of Patent: Sep. 15, 2020

(54) SYSTEM AND METHOD FOR PAIN TREATMENT BY HIGH ENERGY REPETITIVE MAGNETIC FIELDS APPLIED TO A PATIENTS BODY THROUGH SERIALIZED SMART COILS CONTROLLED BY A PROGRAMMABLE PULSE GENERATOR WITH ELECTRONIC PRESCRIPTION VERIFICATION

(71) Applicant: UNIVERSITY OF MARYLAND, COLLEGE PARK, College Park, MD (US)

(72) Inventors: John Robertson Rzasa, College Park, MD (US); Elisabeth Goldwasser, Baltimore, MD (US)

(73) Assignee: University of Maryland, College Park, College Park, MD (US)

( * ) Notice: Subject to any disclaimer, the term of this patent is extended or adjusted under 35 U.S.C. 154(b) by 261 days.

(21) Appl. No.: 15/789,039

(22) Filed: Oct. 20, 2017

Related U.S. Application Data

(60) Provisional application No. 62/410,637, filed on Oct. 20, 2016.

(51) Int. Cl.
*A61N 2/02* (2006.01)
*A61N 2/00* (2006.01)
*G06K 19/07* (2006.01)

(52) U.S. Cl.
CPC .............. *A61N 2/008* (2013.01); *A61N 2/02* (2013.01); *G06K 19/0723* (2013.01)

(58) Field of Classification Search
CPC .................................................. A61N 2/00–12
See application file for complete search history.

(56) References Cited

U.S. PATENT DOCUMENTS

| 9,812,246 B1* | 11/2017 | Nunez | H01F 27/2823 |
| 2010/0228075 A1* | 9/2010 | Lu | A61N 2/008 600/13 |
| 2015/0190648 A1* | 7/2015 | Fischell | A61N 2/006 600/14 |

* cited by examiner

*Primary Examiner* — Thaddeus B Cox
(74) *Attorney, Agent, or Firm* — Rosenberg, Klein & Lee

(57) ABSTRACT

Subject system generates high energy short duration repetitive magnetic fields controlled by a programmable pulse generator. The magnetic fields are applied to a patient's body through a smart coil attachment provided with a sensor system and microcontroller for monitoring the system's health. The novel security architecture and networking components support the electronic prescription concept which ensures a patient receives correct treatment on the prescribed pulse generator with the prescribed coil attachment. An FPGA-based pulser controller operates to control charging of large capacitors (in the pulse generator) to a desired voltage and discharging them through the smart coil attachment to generate the therapeutic magnetic pulses in accordance with the electronic treatment prescription protocol.

20 Claims, 20 Drawing Sheets ic fields may be used to alleviate pain in various parts of a patient's body as a safe alternative to various pain medications which typically may cause negative side effects.
SYSTEM AND METHOD FOR PAIN TREATMENT BY HIGH ENERGY REPETITIVE MAGNETIC FIELDS APPLIED TO A PATIENTS BODY THROUGH SERIALIZED SMART COILS CONTROLLED BY A PROGRAMMABLE PULSE GENERATOR WITH ELECTRONIC PRESCRIPTION VERIFICATION

REFERENCE TO THE RELATED APPLICATIONS

This Utility Patent Application is based on the Provisional Patent Application Ser. No. 62/410,637 filed on 20 Oct. 2016.

FIELD OF THE INVENTION

The present invention is directed to medical systems, and particularly to systems for treatment of pain through delivery of therapeutic magnetic pulses to a patient's body.

The present invention is further directed to a system monitoring the system's health and providing increased safety for a user, which operates with a programmable pulse generator sub-system which controls generation of magnetic pulses by an electro-magnetic coil attached to a respective part of a patient's body to alleviate pain.

The present invention is also directed to a system and method for generation of high energy short duration repetitive magnetic fields under control of a programmable pulse generator capable of electronic prescription verification.

Furthermore, the present invention is directed to a system applying prescribed magnetic fields to a patient's body to treat pain through a "smart" (or "intelligent") coil attachment sub-system contoured to anatomically conform to a respective part of a patient's body and operating with a sensor system and a microcontroller embedded in the "smart" coil attachment in communication with a programmable pulse generator for monitoring operational health of the coil attachment and for diagnostic purposes, as well as for maintaining safety for a user during the prescribed treatment.

In addition, the present invention is directed to a system and method that is capable of high speed efficient charging of large capacitors to a desired voltage and subsequently discharging them through a specialized coil attached to a patient's body in accordance with a treatment prescription protocol entered in the system from an electronic prescription card (E-script card) provided to a patient by medical personnel.

The present invention is further directed to a programmable pulse generator system which cooperates with a "smart" coil attachment secured (but easily removable) to (from) the patient's body during the treatment. Each coil attachment is equipped with an embedded microcontroller and a system of sensors (such as, for example, temperature sensor, accelerometer, and others), where the microcontroller acquires the sensors' readings during the treatment to monitor various parameters of the coil attachment operation, such as, for example, whether the coil attachment is connected, which type (serial number) of the coil attachment is connected, the temperature of the coil, the vibration generated by the coil, etc., in order to monitor the operational health of the coil attachment, and to prevent patient discomfort.

The present invention is also directed to a programmable pulse generator/smart coil attachment system for pain treatment which is configured for verification of the treatment prescription protocol to be used, user identification, coil identification, and pulse generator identification. The system is equipped with a wireless or wired network interface for connection to the Internet/Ethernet to communicate with a medical office to update electronic prescriptions remotely, as well as to communicate with a central facility to monitor the system's health, detect fraud, schedule warranty service and remotely control the pulse generator itself when necessary.

BACKGROUND OF THE INVENTION

Magnetic fields may be used to alleviate pain in various parts of a patient's body as a safe alternative to various pain medications which typically may cause negative side effects.

Numerous generator systems for creating therapeutic magnetic pulses have been developed and used for pain treatment. For example, an electrical pulse generator designed to create magnetic pulses for the treatment of pain is described in U.S. patent application Ser. No. 14/304,309, "Transcutaneous Magnetic Stimulation for the Treatment of Pain", filed 13 Jun. 2014, which is incorporated herein by reference; as well as in U.S. Patent Application Publication No. 2015/0360045, "Electrical Pulse Generator to Create Magnetic Pulses for the Treatment of Pain", filed 3 Jul. 2014.

A number of other systems for delivery of magnetic pulses for treatment of pain have been adopted for the treatment of foot pain caused by chemotherapy or diabetic neurotherapy, shoulder pain, lower back pain caused by numerous medical problems, etc., as well as migraine headaches.

None of the existing systems generating magnetic fields for treatment of pain are known to be able to electronically verify a prescribed treatment protocol prior to initiating the therapeutic procedure, or to authenticate the system to be used, or to use "smart" coils which would monitor the system operational parameters, control the charge/discharge characteristics of a capacitor to vary the magnetic pulses parameters, respond to monitored parameters (such as, for example, coil temperature), and provide increased patient safety.

The present system is a further development in the field of pain alleviation through safe delivery of dynamically controlled magnetic fields which is supported by a novel security architecture and networking components to implement the electronic prescription concept which ensures that a patient receives the correct treatment on the prescribed pulse generator with the prescribed coil attachment, and which prolongs the system's functionality and efficacy.

SUMMARY OF THE INVENTION

It is therefore an object of the present invention to provide a system and method for generating high energy repetitive magnetic fields controlled by a programmable pulse generator with electronic prescription verification capability which provides a medical treatment that is by prescription only.

Another object of the present invention is to provide a pain alleviating system through application of controlled magnetic pulses where a programmable pulse generator controls the magnetic pulses generation by the digital on-demand variation of the capacitor charge voltage by the FPGA (Field-Programmable Logic Array)-based controller embedded in the programmable pulse generator which controls the SCR (Silicon Controlled Rectifier) discharge characteristics at run-time of the system for control of the capacitor's discharge pulse shape. This provides various modes of operation (placebo mode, ramping mode, alternate high/low power pulses, etc.) within the limitations of the electronic prescription for the treatment protocol entered in the FPGA-based controller from an E-script card containing such information.

It is a further object of the present invention to provide a system and method for treatment of pain through delivery of controlled magnetic pulses to a patient's body which is equipped with a sub-system of "smart" coil attachments (each coil attachment being anatomically adapted for a body part to be treated), where each coil attachment is provided with a microcontroller embedded in its housing alongside a system of sensors, including a temperature sensor, accelerometer, and potentially any sensor needed for monitoring and supporting operational health of the system. The sensors are polled by the FPGA-based controller embedded in the programmable pulse generator to monitor different operational parameters of the smart coil attachment, as well as to prevent patient discomfort.

It is another object of the present invention to provide a system and method for generating controllable magnetic fields applied to the patient's body to treat pain which includes a system/user interface configured with a color touchscreen display that changes its appearance based on a variety of situational and operational parameters, such as, for example, a particular user, the coil attachment type, treatment specifics, elapsed time, location (hospital, clinic, home), language, etc., and which can be modified to incorporate any additional scenarios as necessary. The screen also displays various indicia corresponding to the system's operational health, different fault conditions, misuse outside the electronic prescription, etc.

It is an additional object of the present invention to provide a magnetic pulse generating system for the alleviation of pain equipped with a network interface (wired or wireless) which connects the pulse generator to the Internet/Intranet to communicate with a medical office to update the electronic prescriptions remotely, as well as with a Central Diagnostic Facility to gather diagnostic data and monitor system health, detect fraud, schedule warranty service, remotely control the pulse generation itself, if necessary, etc.

In one aspect, the present invention is directed to a system with electronic prescription verification capability for controllable generation of magnetic pulses for pain treatment. The subject system is equipped with the following structural and processor sub-systems:

(a) at least one intelligent coil attachment;
(b) a programmable pulse generator sub-system, and
(c) an electronic prescription card (E-script card) configured with memory storage containing a treatment prescription protocol, a first serial number indicative of a programmable pulse generator to be used, and a second serial number indicative of a coil attachment to be used for the prescribed treatment.

The intelligent coil attachment has a housing contoured in anatomical conformity to a patient's body part to be treated. The coil attachment also includes:

an electromagnetic coil,
a sensor sub-system operatively coupled to the electromagnetic coil, and
a microcontroller (also referred to herein as a coil attachment control sub-system) operatively coupled to the sensor sub-system. The coil attachment control sub-system is configured with a memory storage containing the coil attachment's identification information pre-programmed therein.

The electromagnetic coil, sensor sub-system, and coil control sub-system reside within the coil attachment's housing which is contoured in anatomical conformity to a body part to be treated.

The programmable pulse generator sub-system is equipped with:

at least one capacitor operatively coupled to the coil embedded in the coil attachment (the current pulse generated as the result of the capacitor's discharge is supplied to the electromagnetic coil residing in the coil attachment's housing, which, in turn, generates magnetic pulses used to treat pain);
a capacitor charger circuit operatively coupled to the capacitor(s) to control the capacitor(s)' charge/discharge characteristics,
a FPGA (Field-Programmable Logic Array)-based pulser control sub-system operatively coupled to the capacitor charger circuit and the coil control sub-system. The pulser control sub-system is configured to control the capacitor charger circuit to produce a controllable discharge by the capacitor(s), which results in generation of controlled variable magnetic pulses by the electromagnetic coil residing in the coil attachment housing. The pulser control sub-system includes memory storage containing the programmable pulse generator's identification information.

The programmable pulse generator further is equipped with an RFID (Radio Frequency Identification) transceiver operatively coupled to the pulser control sub-system, which is configured to read the information pre-stored in the electronic prescription card and to transmit this information to the pulser control sub-system for further processing.

The pulser control sub-system is further configured to verify correspondence of the first serial number and the second serial number (obtained by the RFID transceiver from the electronic prescription card) to the coil attachment's identification information received from the coil control sub-system and the pulse generator's identification information contained in its memory storage, and to actuate the treatment protocol in strict correspondence to the treatment prescription protocol read from the E-script card if the authentication has been established, i.e., the verification of the system's parts (coil attachment and pulse generator) has been found.

Otherwise, the pulser control sub-system denies the actuation of the treatment prescription protocol if the verification fails.

The programmable pulse generator uses an FPGA module residing in the pulser control sub-system. The FPGA module is configured to process the information obtained from the electronic prescription card and to generate corresponding control signals supplied to the capacitor charger circuit to adjust charging of the capacitor to a charging voltage corresponding to a required variable output power of magnetic pulses of interest in accordance with the treatment prescription protocol read from the E-script card.

The subject system further includes a system-user interface sub-system which is configured with a reconfigurable display which is operatively coupled to the pulser control sub-system and is configured to display various types of information under control of the pulser control sub-system.

The display includes a color touchscreen and a system of functional buttons for a user to enter various input commands which are supplied to the pulser control sub-system for subsequent processing therein. This results in corresponding control actions applied to the capacitor charger circuit to vary the discharge parameters of the capacitor, and consequently to control magnetic pulses characteristics.

The sensor sub-system may include temperature sensor (s), accelerometer sensor(s), and potentially other applicable sensors as well. The coil control sub-system (microcontroller) acquires the readings of the sensors and transmits the readings to the pulser control sub-system (along with the ID of the attached coil) to monitor operational characteristics of the coil attachment in the process.

The pulser control sub-system is configured to adjust the operation of the capacitor charger circuit in accordance with the monitored operational characteristics of the coil attachment used in the treatment.

The subject system further includes a network interface operatively coupled to the programmable pulse generator, and, specifically, to the pulser controller sub-system via the RFID transceiver. The network interface serves to transmit the operational characteristics (obtained from the sensors in the smart coil attachment) from the pulser controller sub-system to a remote facility to gather diagnostic information and remotely monitor and maintain the system's operational health, as well as to communicate with a remote medical office to remotely control (vary) the treatment prescription protocol pre-programmed in the electronic prescription card (E-script card) from the medical office through the network interface.

The subject system further includes a number of protection circuits. For example, an emergency protection circuit is coupled to the capacitor and resides next to the capacitor charger circuitry board. The emergency protection circuit includes a series connected switch and resistor coupled in parallel to the capacitor. The switch shorts the capacitor through the resistor to dissipate the energy of the capacitor if a lid of the pulse generator is opened.

The capacitor charger circuit is a high speed capacitor charger circuit which includes a digital potentiometer controlled by the pulser control sub-system to adjust a feedback resistor which in turn adjusts the capacitor charge voltage set-point in accordance to the user's input commands for the desired power level of the magnetic pulses.

Preferably, the capacitor is a polymer film capacitor. The capacitor charger circuitry further includes pulse forming circuitry, which is built with a transformer operatively coupled to the capacitor, and a SCR coupled to the pulse transformer. The pulse transformer operates to build up energy to generate a sufficient current pulse to open the SCR. The SCR is remotely triggered by the pulser control sub-system to generate the magnetic pulse in the coil attachment by shorting the capacitors through the coil to ground.

In another aspect, the present invention constitutes a method for controllable generation of magnetic pulses for pain treatment. The subject method comprises the steps of:
providing at least one intelligent coil attachment with a housing contoured in anatomical conformity to a patient's body part to be treated,
operatively coupling a sensor sub-system to an electromagnetic coil in the coil attachment's housing, and
configuring a coil control sub-system with memory storage containing the coil attachment's identification information pre-programmed therein, and embedding the coil control sub-system in the coil attachment in operative coupling to the sensor sub-system.

The method further comprises the following steps:
establishing a programmable pulse generator sub-system equipped with:
at least one capacitor operatively coupled to the coil embedded in the coil attachment, and
a capacitor charger circuitry operatively coupled to the capacitor.

The method also includes the steps of:
configuring a pulser control sub-system to control the capacitor charger circuitry to produce a controllable discharge by the capacitor to result in generation of controlled variable magnetic pulses by the electromagnetic coil,
embedding the pulser control sub-system with memory storage and recording the pulse generator's identification information in its memory storage, and
operatively coupling the pulser control sub-system to the capacitor charger circuitry and the coil attachment control sub-system.

The subject method further contemplates:
coupling an RFID transceiver to the pulser control sub-system, and
providing an electronic prescription card (E-script card) configured with memory storage containing a treatment prescription protocol, a first serial number indicative of a programmable pulse generator to be used, and a second serial number indicative of a coil attachment to be used.

In the subject method, the pulser control sub-system further performs the procedure for verification of correspondence of the first serial number and the second serial number read by the RFID transceiver from the electronic prescription card to the pulse generator's identification information contained in its memory storage and the coil attachment's identification information received from the coil attachment control sub-system, respectively. When the pulse generator and the coil attachment are authenticated (verified) for the prescribed treatment protocol, the pulse generator permits actuation of the treatment in correspondence to the treatment prescription protocol read from the E-script card.

If, however, the authentication procedure fails (no match is found), the pulser control sub-system denies actuation of the treatment.

The subject method further continues by embedding an FPGA module in the pulser control sub-system, and configuring the FPGA to process the information obtained from the electronic prescription card to generate corresponding control signals supplied to the capacitor charger circuitry to adjust charging of the capacitor to a charging voltage corresponding to the required output power of magnetic pulses of interest in accordance with the treatment prescription protocol.

The subject method further is enhanced with establishing a system-user interface which is configured with a reconfigurable color touchscreen display operatively coupled to the pulser control sub-system and configured to display various kinds of information under control of the pulser control sub-system. A system of functional buttons is provided for a user to enter various input commands. In the subject method, the entered commands are supplied to the pulser control sub-system for subsequent processing therein and control of the capacitor charger circuitry in correspondence to the input commands.

The method further includes the following steps:
operatively coupling sensors (such as, for example, a temperature sensor, an accelerometer sensor, and other applicable sensors) to the electromagnetic coil,
acquiring the readings of the sensors by the coil control sub-system, and transmitting the readings of the sensors to the pulser control sub-system to monitor operational characteristics of the coil attachment.

In the subject method, the pulser control sub-system is further configured to adjust the operation of the capacitor charger circuitry in accordance with the monitored operational characteristics of the coil attachment.

The present method further includes the steps of:
operatively coupling a network interface to the programmable pulse generator,
transmitting the monitored operational characteristics through the network interface to a remote facility to gather diagnostic information and remotely monitor the subject system's operational health, and
optionally, to re-program the treatment prescription protocol in the electronic prescription card remotely from a medical office through the network interface.

These and other objects of the present invention will become obvious in view of the Detailed Description of the subject invention considered in conjunction with the Patent Drawings presented herein.

DETAILED DESCRIPTION OF THE PREFERRED EMBODIMENT(S)

The subject system is configured for pain alleviation through the non-invasive therapeutic treatment of human and animal patients. The subject system utilizes a programmable pulse generator circuitry cooperating with an intuitive user interface and "smart" coil assembly (coil attachment) to supply rapid pulses of current from the pulse generator to an electromagnetic coil in the coil attachment, thereby producing pulsed magnetic fields by the electromagnetic coil to be directed towards a distressed area in a patient's body, resulting in temporary or permanent relief of pain in the patient.

Figure 1:
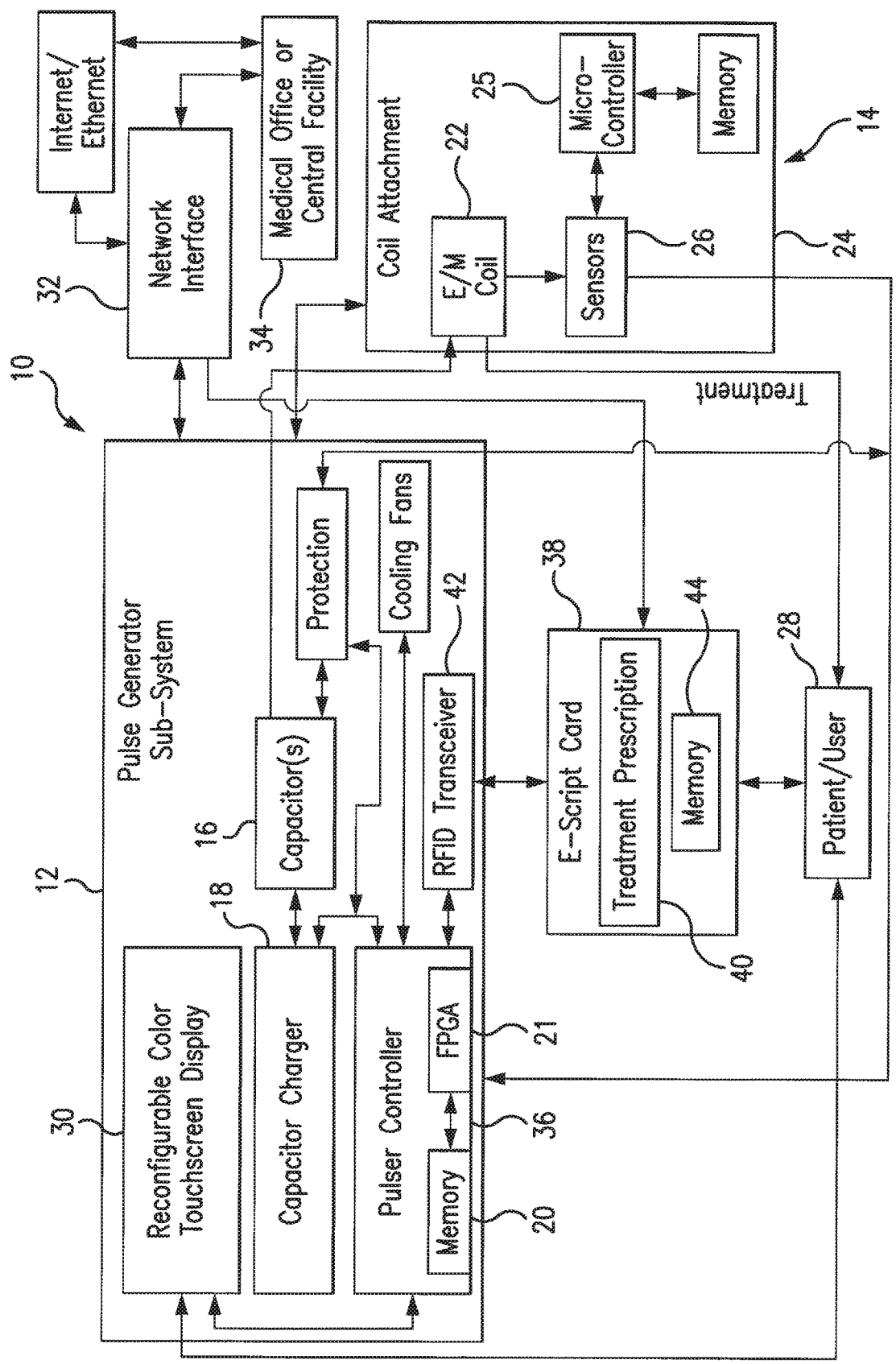
FIG. 1 is a schematic representation of the present system for treatment of pain through application of controllable magnetic pulses.
Figure 2:
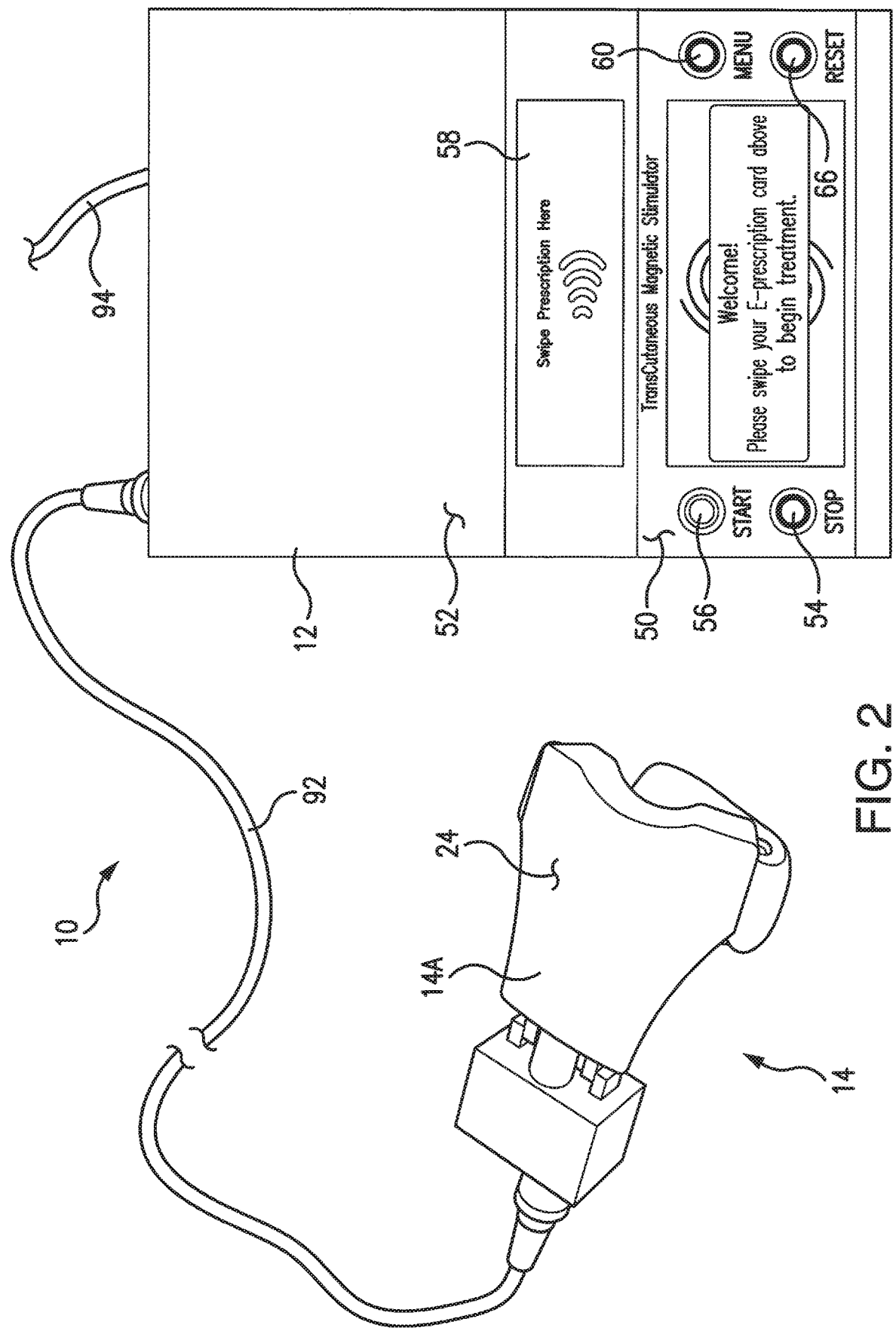
FIG. 2 is a representation of the front view of the programmable pulse generator coupled through the cable with a "smart" coil attachment.
Figure 3:
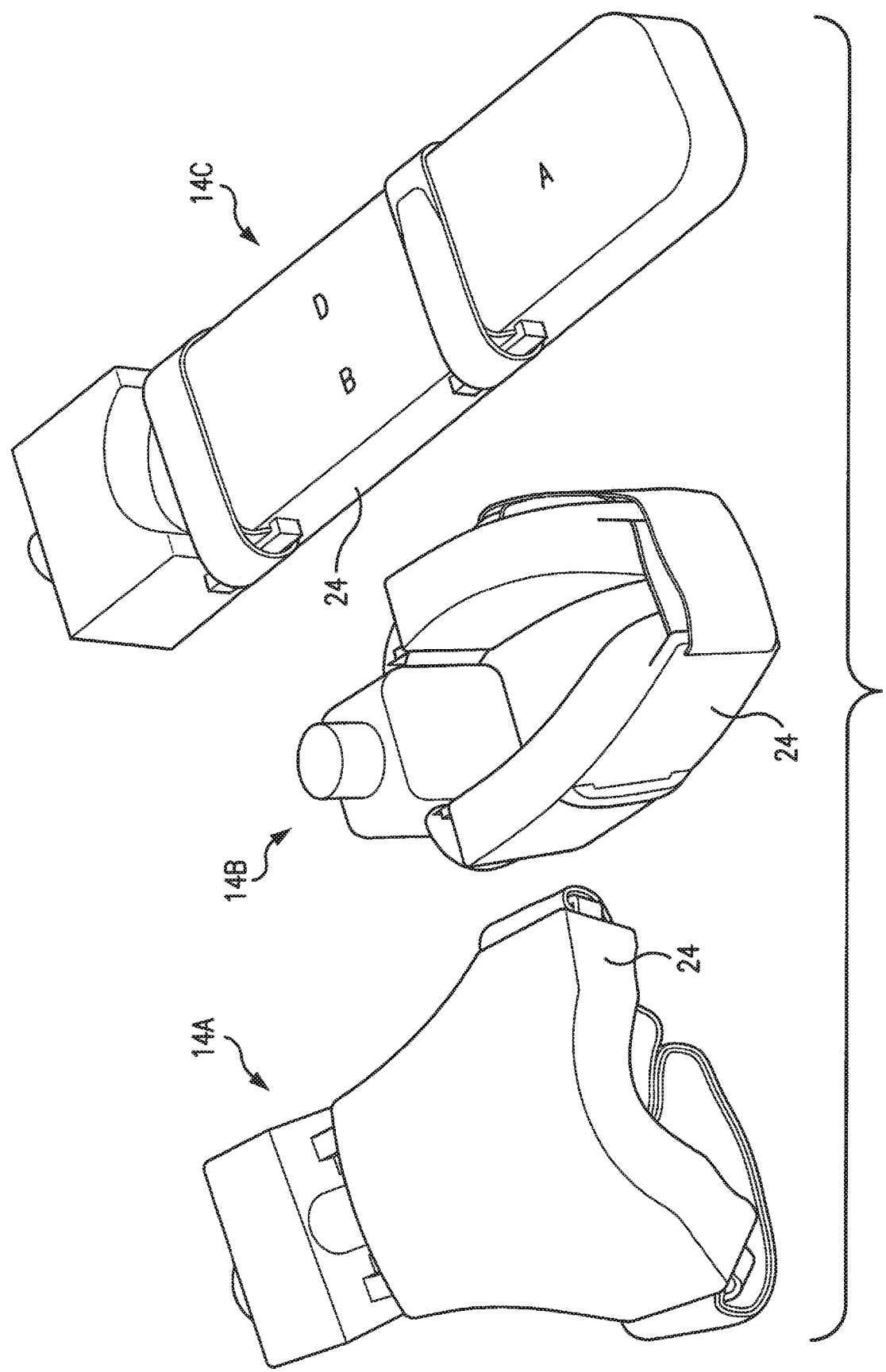
FIG. 3 depicts perspective views of subject coil attachments contoured to anatomically conform to different parts of a patient's body.

Referring to FIGS. 1-3, the subject system 10 is designed for pain treatment on a patient through application of high energy short duration repetitive magnetic fields to a distressed area in a patient's body through a serialized smart coil attachment. The generation of magnetic fields is controlled by a programmable pulse generator sub-system 12 configured with electronic prescription verification capabilities.

The subject system 10 includes one or a number of removable coil attachment sub-systems 14 which are connected with the programmable pulse generator sub-system 12, and attached (removably) to a part of patient's body to deliver magnetic pulses thereto during a therapeutic procedure.

As shown in FIGS. 2 and 3, the coil attachment sub-system 14 may be presented in variety of configurations, depending on a portion of the patient's body to be applied to. For example, as shown in FIGS. 2-3, the coil attachment 14A is configured for application to the top of a foot, and thus is contoured in anatomical conformity to a patient's foot. Shown in FIG. 3, a coil attachment 14B is configured for treatment of an ankle or a shoulder of a patient, and thus is contoured in anatomical conformity to these parts of the body. Also, as shown in FIG. 3, a coil attachment 14C is configured for treatment of the bottom of a foot, and thus is contoured in anatomical conformity to the bottom of a foot.

It is to be understood that the configurations of the coil attachments 14A, 14B, and 14C shown in FIGS. 2 and 3 are merely exemplary embodiments, and other alternative configurations are contemplated in scope of the present invention, which may be adapted to different parts of a patient's body.

As presented in FIGS. 1, 2, 4A-4B, 5, 7, 8A-8K, and 9-10, the pulse generator sub-system 12 includes a capacitor 16 (or a system of inter-connected capacitors) which is (are) charged to a desired voltage and subsequently discharged (under the control of the capacitor charger circuitry 18, also referred to herein as a capacitor charger control circuitry) through the coil attachment 14 in use. The capacitor charger control circuitry 18 is based on a switched-mode capacitor charger chip topology (for example, from Linear Technologies) which was modified for the subject system to permit digital on-demand variation of the capacitor 16 charge voltage by a FPGA (Field Programmable Logic Array)—based Pulser Controller sub-system 20 that is configured to control the capacitor's discharge (amplitude of the discharge, the mode of operation), as well as operation of the entire system 10.

The digital on-demand variation of the capacitor charge voltage through the FPGA's control assumes different treatment modes to be used at a run-time, including placebo mode, ramping modes, alternate high/low power pulses, etc. The FPGA-based Pulser Controller sub-system 20 also is configured to control characteristics of the SCR (Silicon Controlled Rectifier) 104 (shown in FIGS. 9-10) at run-time for control of the discharge pulse shape (as will be detailed in the following paragraphs).

The specifics of the capacitor charger control circuitry 18 will be presented in the following paragraph in conjunction with discussion of FIG. 9, as well as the schematic diagram of the high voltage board and chassis shown in FIG. 10, and the schematic diagram of the Pulser control board 20, shown in FIG. 11, which are embedded in the programmable pulse generator sub-system 12.

Each coil attachment 14 includes an electromagnetic coil 22 operatively coupled to the capacitor 16 residing in the Pulse Generator sub-system 12. The electromagnetic coil 22 generates magnetic fields in accordance with the capacitor's discharge under control of the capacitor charger control circuitry 18.

Each coil attachment 14 (14A, 14B, 14C) has a housing 24 contoured to adapt the anatomical shape of the body part to be treated. Embedded in the housing 24, in addition to the electronic coil 22, is a microcontroller 25, also referred to herein as a coil attachment controller sub-system, and a system of sensors 26, detailed in the following paragraphs in conjunction with the schematic diagram of the coil attachment shown in FIG. 13.

The system of sensors 26 may include a temperature sensor, an accelerometer, and potentially any other applicable sensor. The microcontroller 25 acquires the readings of the sensors 26 and processes them to transmit to the Pulser Controller 20.

Alternatively, the sensors 26 (when the coil attachment 14 is connected to the programmable pulse generator 12) may be polled directly by the FPGA-based Pulser Controller 20 to monitor numerous operational parameters and situations, and any information related to the coil attachment functionality, including (but not limited to): a) whether the coil attachment is connected to the pulse generator sub-system 12, b) which type and serial number of the coil attachment is connected, c) the temperature of the coil 22, d) the vibrations generated by the coil 22, and other operational and situational parameters.

The temperature of the coil and the vibration generated by the coil 22 are essential for monitoring the health of the coil attachment sub-system 14 and for preventing patient 28 discomfort.

The coil attachment sub-system 14 constitutes a "smart" (or "intelligent") sub-system that is beneficial for monitoring and maintaining the long-term health and operational success of the subject system 10.

Figure 13:
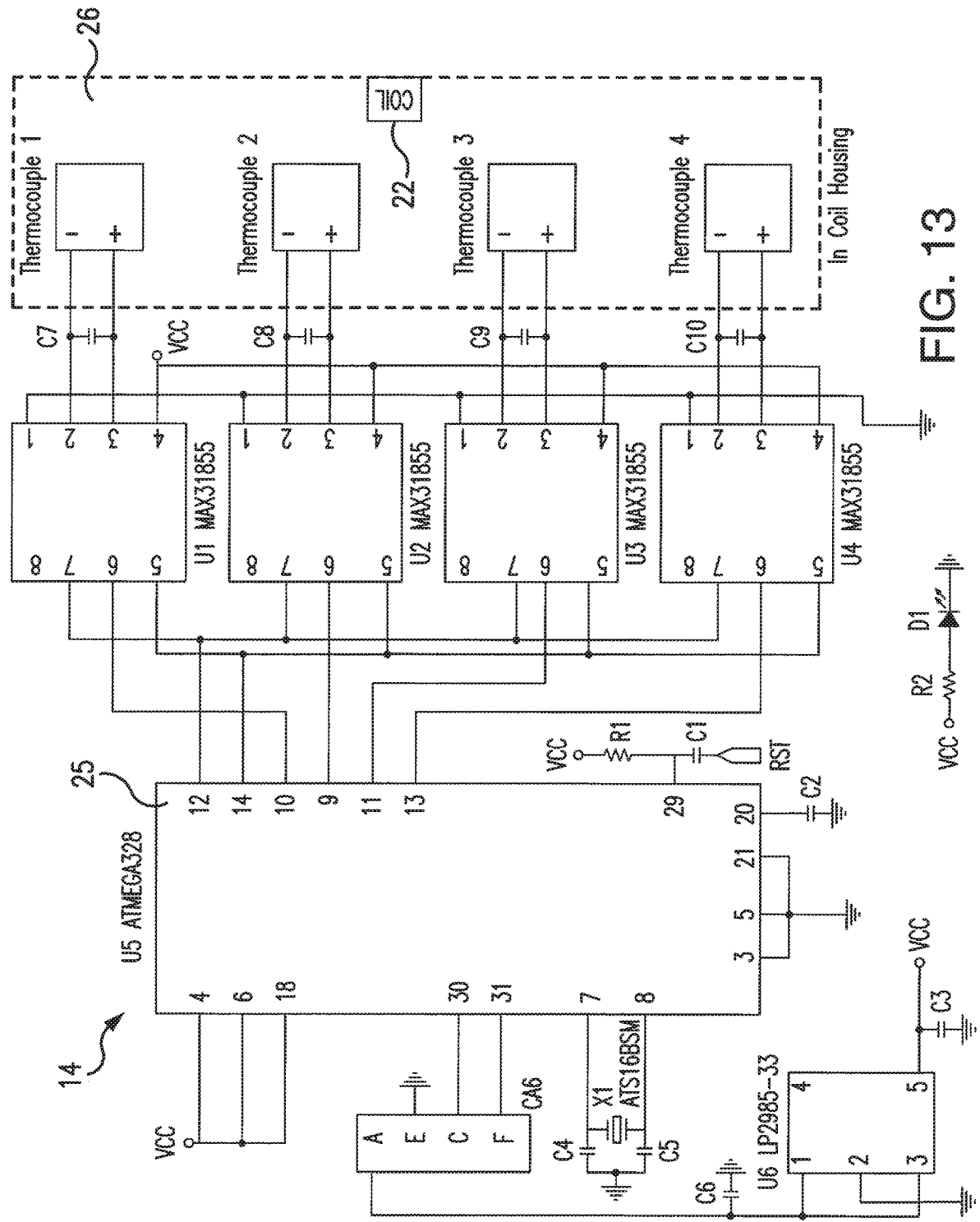
FIG. 13 is a schematic diagram of the coil sensor circuitry embedded in the smart coil attachment.

The schematics of the "smart" coil attachment 14, including the microcontroller 25 and the system of sensors 26, is detailed in FIG. 13.

Depending on the operational characteristics of the coil attachment 14, monitored by the microcontroller 25 and the Pulser Controller 20, different amounts of energy are to be delivered from the capacitor 16 to the electromagnetic coil 22 to achieve the prescribed magnetic field strength.

This adjustment of the energy level to accommodate the prescribed treatment protocol is executed by the Pulser Controller sub-system 20 which processes the sensor's readings and adjusts the operation of the capacitor charger control circuitry 18 accordingly.

As shown in FIGS. 1, 2, 5, 8A-8K, 9 and 12, the pulse generator sub-system 12 is equipped with a reconfigurable color touchscreen display 30 that changes its configuration based on numerous operational and situational parameters, including (but not limited to): a particular user, coil attachment type, treatment protocol specifics, elapsed time to the end of the treatment, etc. The appearance of the display 30 is adaptively changed also based on location (hospital, clinic), user (doctor at the clinic, or patient at home), language, treatment type (back, shoulder, arm, etc.), and may be modified to incorporate any additional scenarios as necessary.

The display screen 30 may also indicate that the system is disabled in case of electronics failure, in a situation when no coil attachment has been connected, a wrong security code/card being entered, or that the coil attachment being used for in regimes outside the prescription, etc. The display screen also may indicate a physical location and change thereof if a cellular communication chip is employed with the subject programmable pulse generator 12.

The front panel display 30 serves as an interface with the user so that a user (doctor or a patient) can enter treatment notes in real-time to gather information about the efficacy, potential problems, and other issues associated with the treatment. The treatment notes entered into the touch screen display 30 can be communicated back to a hospital/clinic server to keep records about the treatment by prescribing doctors, and/or diagnostic hub/central facility as an additional tool for monitoring system health and impending maintenance and upgrades of the system.

The present system 10 operates with a network interface 32 which wirelessly (or wired) connects the pulse generator sub-system 12 to the Internet (Intranet) and permits a remote medical office 34 to update prescriptions remotely. The network interface connection 32 also permits a central facility 34 to gather diagnostics from the programmable pulse generator 12 and monitor system health, detect fraud, schedule warranty service, and remotely control the pulse generator 12 itself, if deemed necessary.

One of the important features of the present system 10 is that it provides a medical treatment that is "prescription only". In order to prevent misuse of the system, the subject system 10 enables a complete electronic prescription, or E-script. The programmable pulse generator sub-system 12 is provided with a non-volatile memory chip 36 residing on the FPGA board 20 or operatively connected thereto. The memory 36 is programmed with a unique serial number for the pulse generator 12.

In addition, the system 10 includes an RFID (Radio Frequency Identification) card, also referred to herein as an E-script card 38, that is provided to the patient 28 (by the medical office 34). The RFID E-script card 38 has a memory storage 44 which contains the patient's prescription treatment protocol, also referred to herein as a treatment prescription 40 which includes the number of treatments, pulses per treatment, power of each pulse, treatment profile (full on, ramp, etc.). The E-script card 38 also stores (in the memory storage 44) the identification (serial number) of the particular pulse generator to be used and the identification (serial number) of the coil attachment to be used (back, shoulder, foot, etc.) for the treatment prescription 40.

The RFID transceiver 42 in the pulse generator sub-system 12 reads the information stored in the memory storage 44 of the E-script card 38 when the patient scans the E-script card 38 against the RFID transceiver 42 provided on the pulse generator 12, as will be detailed in following paragraphs.

The FPGA-based controller sub-system 20 cooperates with the RFID transceiver 42 to receive therefrom the treatment prescription 40 as well as the identification information serial number of the pulse generator and the coil attachment to be used which are pre-programmed in the E-script card 38. The FPGA controller 20 compares the serial numbers of the pulse generator received from the E-card with the serial number pre-recorded in the memory chip 36.

The RFID transceiver 42 also reads from the E-card and transmits to the FPGA pulser controller 20 the information on the type of the coil attachment 14 to be used for the treatment which is included into the E-script card's treatment prescription. The unique microcontroller 25 in each coil attachment 14 provides its identification to the FPGA-based controller 20, The microcontroller 25, in cooperation with the FPGA-based pulser controller 20, thus ensures that only the prescribed coil attachment (the one indicated in the treatment prescription) is used in conjunction with the respective RFID E-script prescription card on the right Pulse Generator 12.

The FPGA-based pulser controller 20 compares all the information (identification information on the pulse generator and coil attachment prescribed to be used for treatment) received from the E-script card through the RFID transceiver with the identification information on the pulse generator recorded in the memory chip 36, and with the identification information on the coil attachment provided from the microcontroller 25, and if the match is found, allows the treatment to begin. Otherwise, the treatment is denied if the authentication of the pulse of the pulse generator and/or coil attachment fails (no verification is made).

Further, after reading the treatment prescription from the E-script card 38, the FPGA pulser controller 20 controls (through control of the capacitor charger controller 18) the discharge of the capacitor 16 accordingly to provide treatment within the limitations of the treatment prescription pre-stored in the E-script card 38.

All information regarding the operation of the system is also logged in the non-volatile memory storage 36, so there is a complete log of the system operation, including invalid attempts of use. This data can also be transmitted to the central facility 34 for monitoring/diagnostic/statistical analysis.

The internal pulse/temperature/power logging used in the subject system ensures that individual components do not exceed their usage specifications to prevent catastrophic damage. For example, the subject system may need high stress parts (such as charge capacitors, flyback diode, bleed-off resistor, coil, etc.) to be replaced after a prescribed number of charge/discharge cycles. This data is also stored in the non-volatile memory storage 36 and may be transmitted to the central facility 34 at regular intervals. If the central facility notices a part is nearing potential failure during the middle of a treatment, it can remotely disable the device to prevent possible harm to the patient.

In addition to the afore-presented measures to maintain the system's health and provide safety for the patient, the subject system 10 includes an emergency capacitor dump button to discharge the capacitor(s) 16 safely if power is lost during a charge cycle to ensure that no charge is remaining before the unit is opened. The details of the emergency protection circuit will be presented in the following paragraph in conjunction with the discussion of FIG. 10.

As shown in FIGS. 2, 5, 8A-8K and 12, a front panel 50 of a housing 52 of the programmable pulse generator 12 includes the attached display panel 30 which illuminates when power is turned "on", and display instructions or progress of treatment.

The front panel 50 also has a Stop button 54 which is used to stop the treatment once the treatment has begun. Once the Stop button has been pressed, an additional pulse will be necessary to discharge the capacitor(s) 16 by pushing the Stop button a second time. This can be done after removing the coil attachment from the patient, or whenever an operator is ready, but before the device is turned OFF or reset.

Start button 56 is presented on the front panel 50 of the housing 52. The Start button is used to start the treatment or to pause the treatment. When the pause feature has been activated, the device will complete the next impending pulse, and subsequently pause.

The front panel 50 of the housing 52 of the programmable pulse generator 12 further includes a prescription card swipe area 58 over which the prescription E-card 38 is to be swiped to activate the system 10.

A Menu button 60 is actuated to confirm that the correct coil attachment is attached to the pulse generator 12 prior to treatment, and to alter settings of the treatment from the standard setting (of, for example, 100 pulses at 100% pulse strength for the duration of 10 minutes).

A Reset button 66 is actuated after actuating the Menu screen on the display 30 to reset any adjusted settings back to the default settings.

Figure 4A:
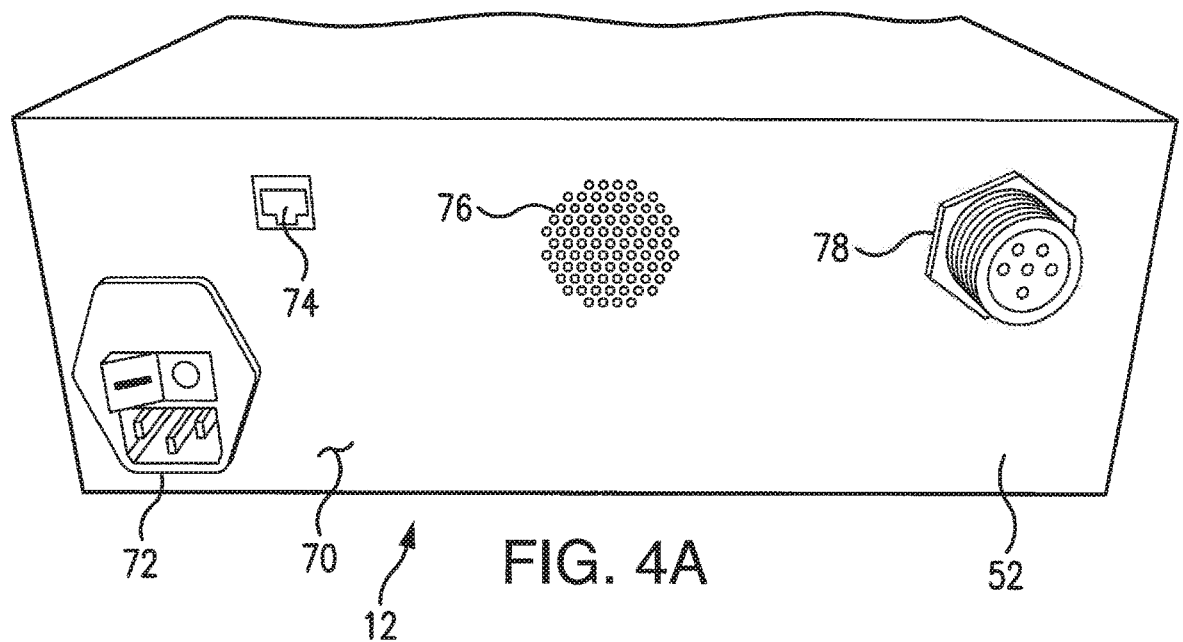
FIGS. 4A and 4B are the back and side views, respectively, of the programmable pulse generator in the subject system.

Shown in FIG. 4A is a rear panel 70 of the housing 52 of the programmable pulse generator 12. As shown in FIG. 4A, the rear panel 70 has a line input assembly 72 which may include the IEC 320-C14 line cord receptacle, instrument power switch, and line fuse holder. Through the line input assembly 72, the pulse generator 12 is connected to a power source (not shown). An Ethernet port 74 on the rear panel 70 is a standard Ethernet port for connection to a computer system or other network hardware.

A cooling fan vent 76 is provided for a 24 VDC cooling fan installed in the housing 52 to maintain a satisfactory temperature within the housing 52. The coil cable input 78 provides a keyed receptacle for the cable connection to the treatment coil attachment 14.

Figure 4B:
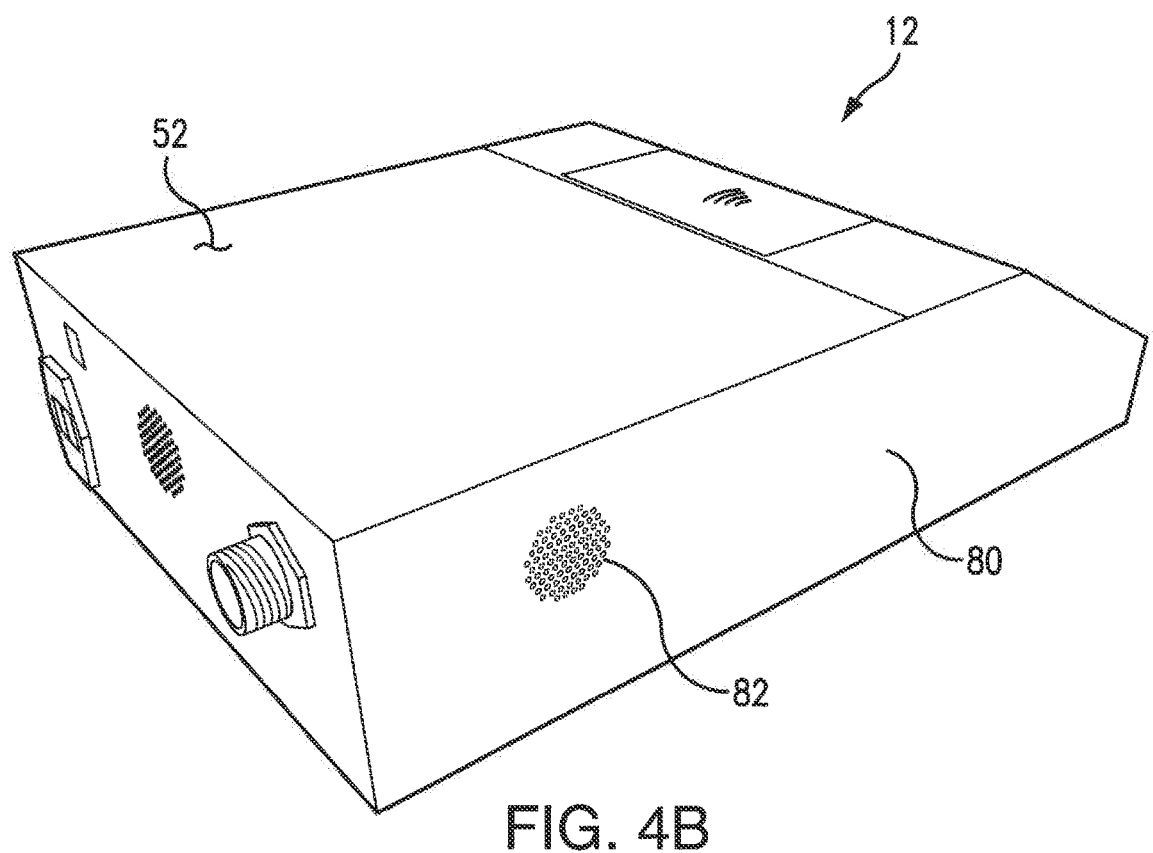

The side panel 80 of the housing 52 of the pulse generator 12 is shown in FIG. 4B. The side panel 80 is presented with the cooling fan vent 82 for a 24 VDC cooling fan residing inside of the housing 52 to maintain a temperature within the housing at a predetermined level.

Figure 5:
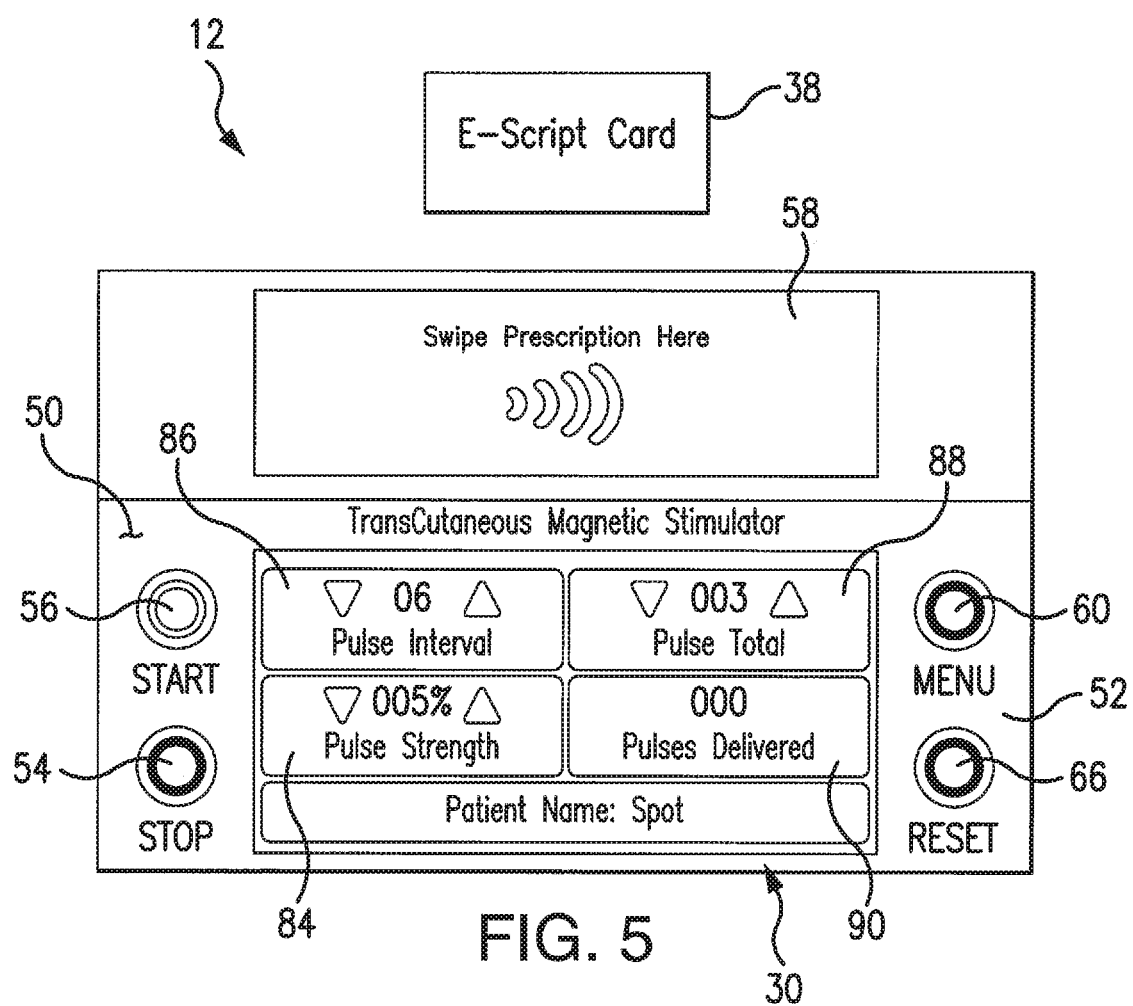
FIG. 5 is a front view of the subject programmable pulse generator showing the reconfigurable color touchscreen display.

Shown in FIG. 5 is the front panel 50 of the pulse generator housing 52 with emphasis on the attached display panel 30. As shown in the icon 84, the attached panel display permits the increase or decrease of pulse strength by pressing the up or down arrows. The pulse strength can range from 0-100%.

The pulse interval setting display screen 86 provides input for an increase or decrease of the pulse interval in seconds by pressing the up or down arrows. The pulse interval may range, for example, between 6-20 seconds.

The pulse total setting display screen 88 permits increase or decrease of the pulse total or number of pulses per treatment by pressing the up or down arrows. The pulse total can range, for example, between 1 and 100 pulses.

The pulses delivered display screen 90 counts pulses delivered (after each pulse is delivered) until the treatment/pulse set is complete. The number of the pulse delivered is equal to the number of pulses set in the pulse total display screen 90 when the treatment is completed.

The RFID prescription card (E-script card) 38 is supplied (mailed or handed) to a patient with each system 10 to unlock the device and to activate the preset treatment settings.

As shown in FIGS. 2 and 4A, for operation, the coil attachment 14 is attached through the coil cable 92 to the coil cable input 78 at the rear panel 70 of the pulse generator's housing 52.

The power cord 94 is plugged into the line input assembly 72 on the rear panel 70, and also into a conventional 115/120 V AC outlet. Subsequent to this operation, the power switch is to be switched to the "on" position.

Figure 6:
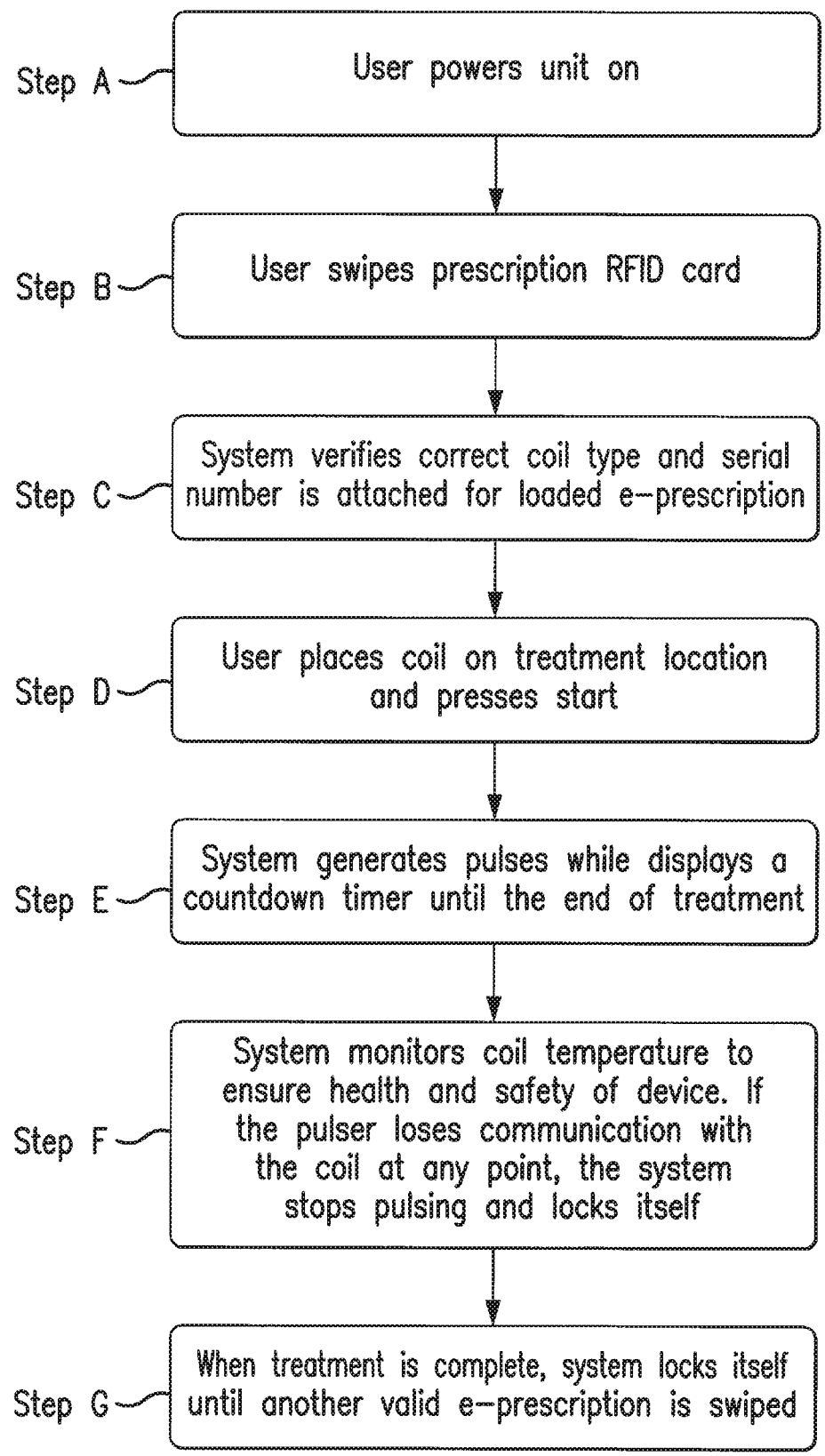
FIG. 6 is a flow chart diagram of the subject system operation.

Referring to FIG. 6, the operation of the subject system 10 begins in Step A, where the user powers the pulse generator 12 ON. The logic further operates to prompt the user to swipe the prescription RFID card in Step B.

Following the information read by the RFID transceiver 42 from the E-script card 38, the logic follows to Step C, where the FPGA controller 20 verifies that the correct coil attachment 14 (coil attachment type and serial number) is attached for the load E-prescription.

In Step D, a user places the coil attachment 14 on the part of the body to be treated and presses the Start button on the front panel of the pulse generator 12.

In the following Step E, the pulse generator 12 generates pulses while displaying a countdown timer on the display 30 until the end of treatment.

In Step F, the system monitors operational characteristics of the coil. The sensors 26 within the coil attachment housing provide readings of the coil temperature and vibration to the microcontroller 25 as well as to the FPGA-based controller (pulse controller) 20 so that system can monitor coil temperature and acceleration to ensure health and safety of the device. If the pulse controller 20 loses communication with the coil attachment at any point during the treatment, the pulse generator 12 stops pulsing and locks itself.

When in Step G, the treatment is complete, the pulse generator 12 locks itself until another E-script card is swiped.

Subsequent to powering the pulse generator 12 in Step A (shown in FIG. 6), the touch panel display 30 will illuminate and boot up. The display 30 cycles through three display screens, including boot-up screens shown in FIG. 8A, and the Stop, Menu, and Reset buttons are illuminated.

Figure 8A:
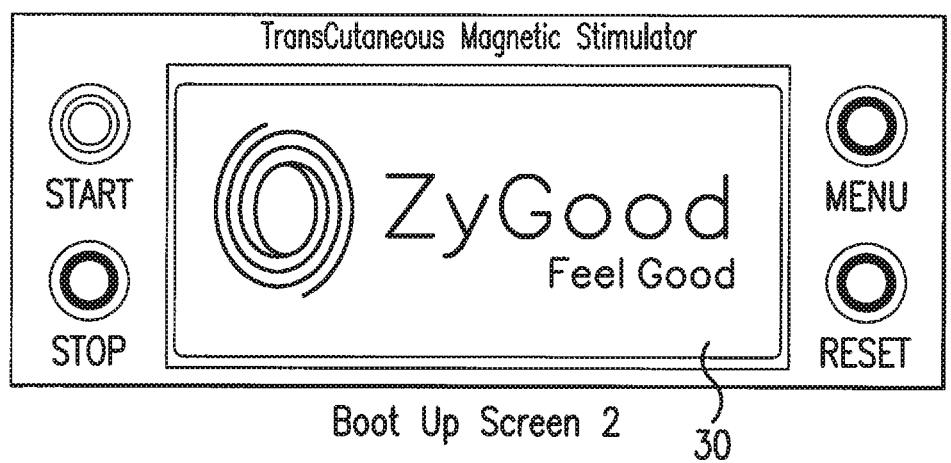
FIGS. 8A-8K show the subject reconfigurable color touchscreen display at different stages of the system operation, with FIG. 8A showing the bootup screen, FIG. 8B showing the instruction on the screen to swipe the RFID prescription card to begin the operation, FIG. 8C showing the display screen with the instruction prompting the user to press the Menu button to confirm that the correct coil is attached, FIG. 8D showing the display screen indicating that the device is ready for the standard treatment (100 pulses at 100% pulse strength for a duration of 10 minutes), FIG. 8E showing the display screen after the menu feature has been selected, FIG. 8F showing the display screen configured for adjusting the settings as desired by attaching the up and down arrows in the respective display portions, FIG. 8G showing the display screen prompting to press the Start button to begin treatment, FIG. 8H showing the time remaining to the end of the treatment, FIG. 8I showing the display screen when the treatment is complete, FIG. 8J showing the display screen in the event that a treatment needs to be paused, FIG. 8K showing the display screen with the instruction in the event that the treatment needs to be stopped unexpectedly.
Figure 8A:
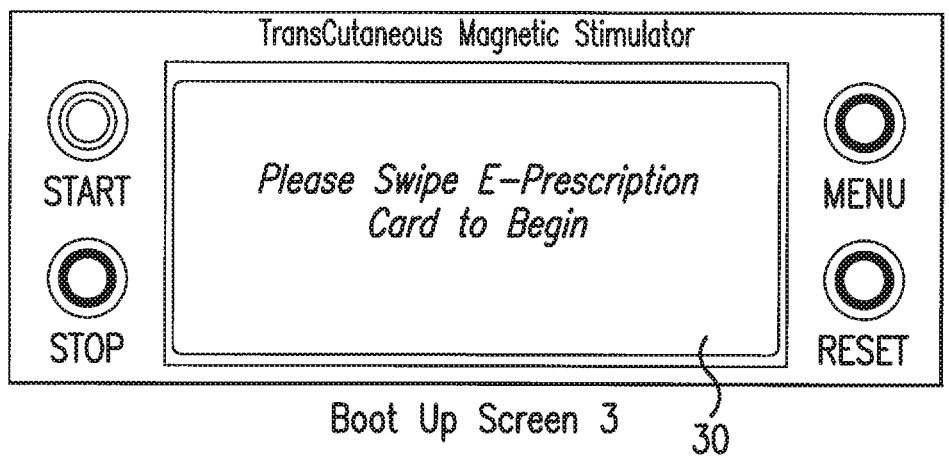
Figure 8B:
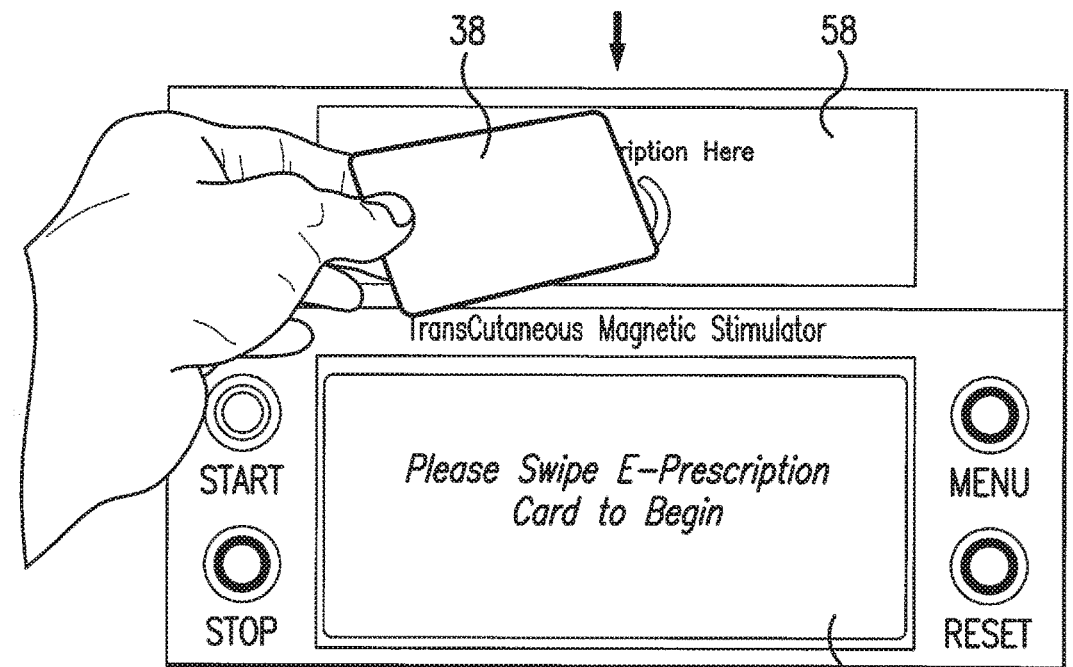
Figure 8C:
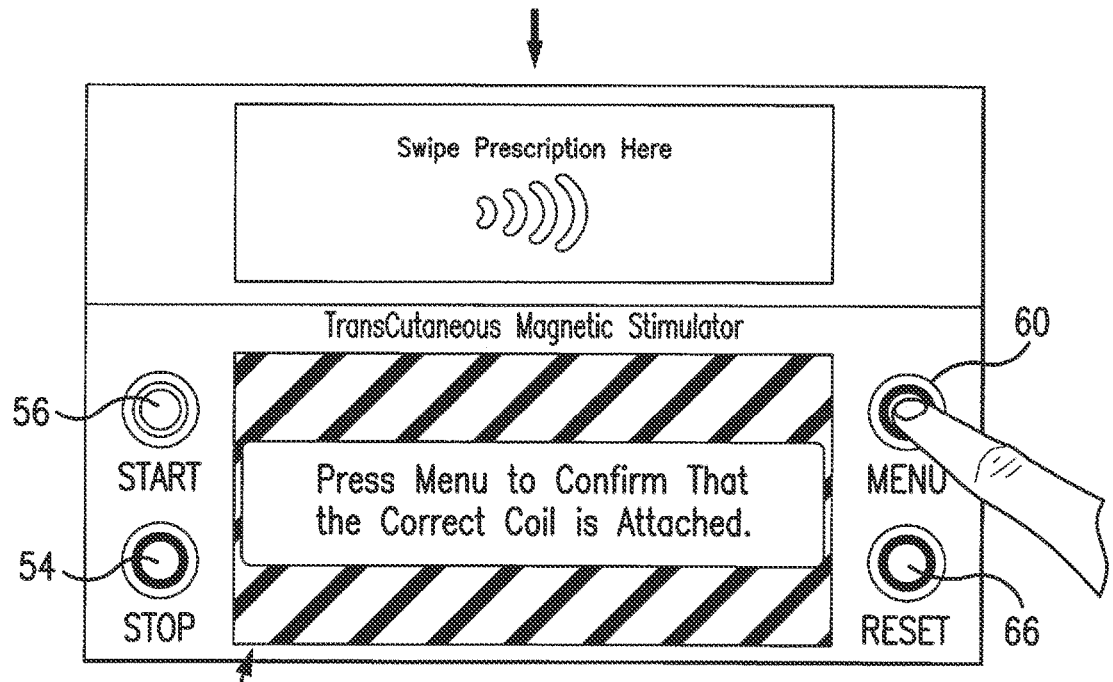

Subsequently, the display screen 30, as shown in FIG. 8B, shows the instruction to swipe the prescription card to begin the treatment procedure, and the user swipes the E-script card in Step B of FIG. 6.

Figure 7:
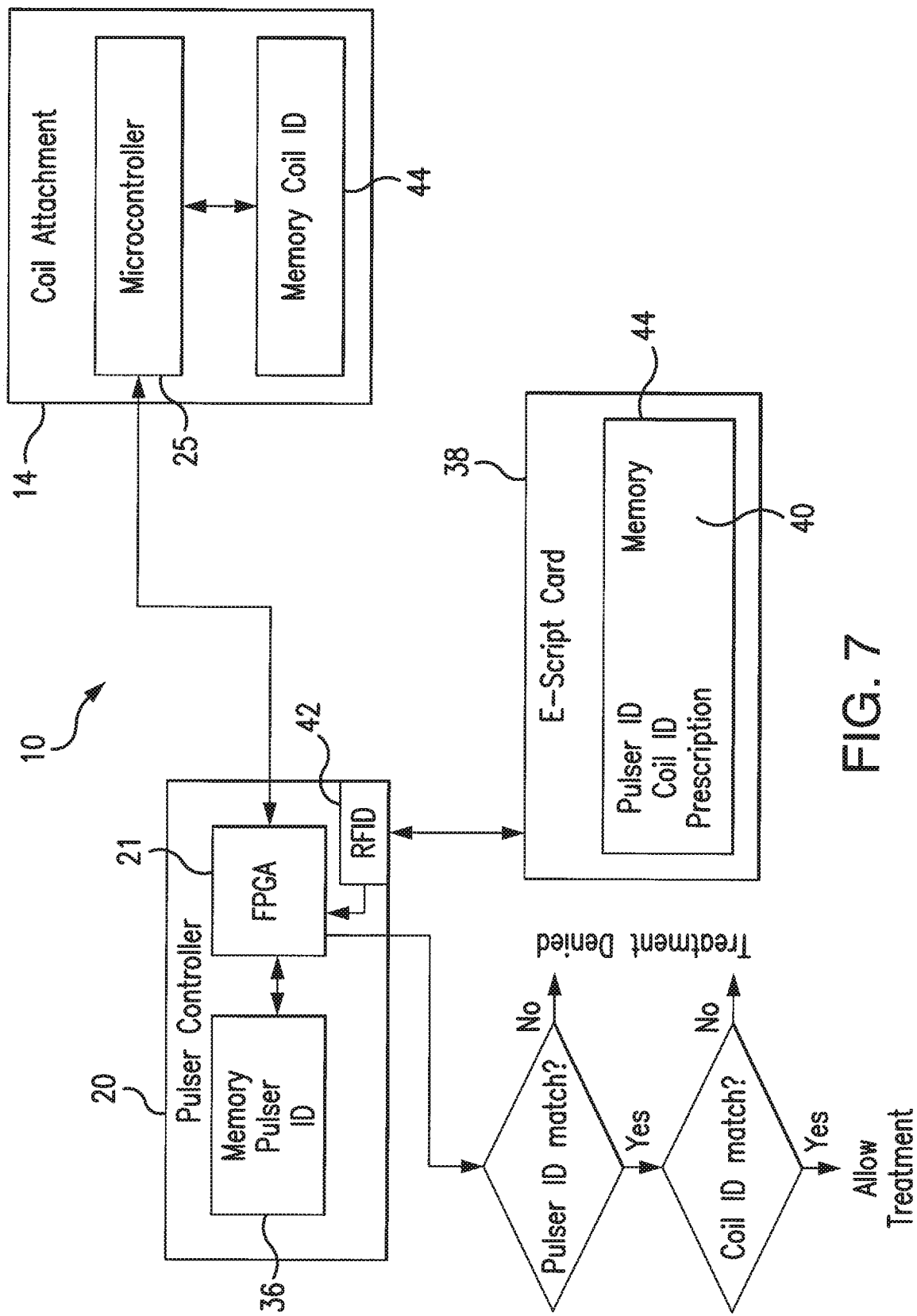
FIG. 7 is a schematic representation of the verification routine executed by the Pulser Controller.

As shown in FIG. 7 and Step C of FIG. 6, subsequent to swiping the E-script card over the prescription card swipe area 58 on the housing 52 of the pulse generator 12, the FPGA-based pulser controller 20 processes the information read by the RFID reader (transceiver) 42 and executes the authentication routine, i.e., verifies if the Pulse Generator's ID in the E-script card matches the Pulse Generator's ID pre-recorded in the NV (non-volatile) memory 36. If the match is found, the FPGA-based pulser controller 20 proceeds to verify whether the coil ID in the E-script card 38 matches the coil ID supplied by the microcontroller 25 of the coil attachment 14. If the match is found (i.e., a correct coil attachment is connected), the FPGA-based Pulser Controller 20 allows the treatment prescribed in the E-script card 38. If, however, a mismatch is identified (verification failed), the pulser controller 20 denies initiation of the treatment.

As shown in FIGS. 6 (Step C) and 8C, the Menu button 60 is pressed to confirm that the correct coil assembly is attached.

Figure 8D:
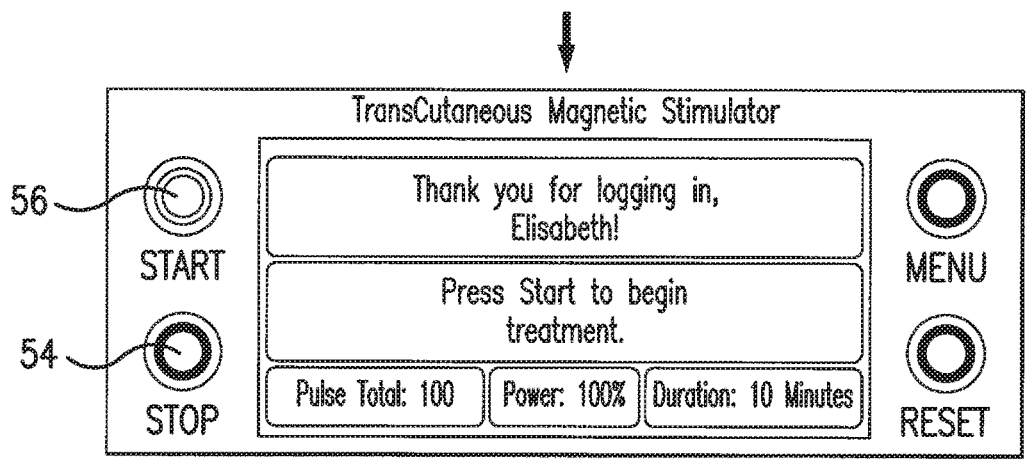

Subsequently, as shown in FIG. 8D, the device is ready for the standard treatment of 100 pulses at 100% pulse strength for a duration of 10 minutes, and the instruction is displayed to press the Start button 56 to begin procedure (Step D of FIG. 6).

In order to start the treatment, the Start button 56 is pressed. In order to adjust the treatment settings, the Menu button 60 is pressed as shown in FIG. 8E, and continue with the instructions.

Figure 8E:
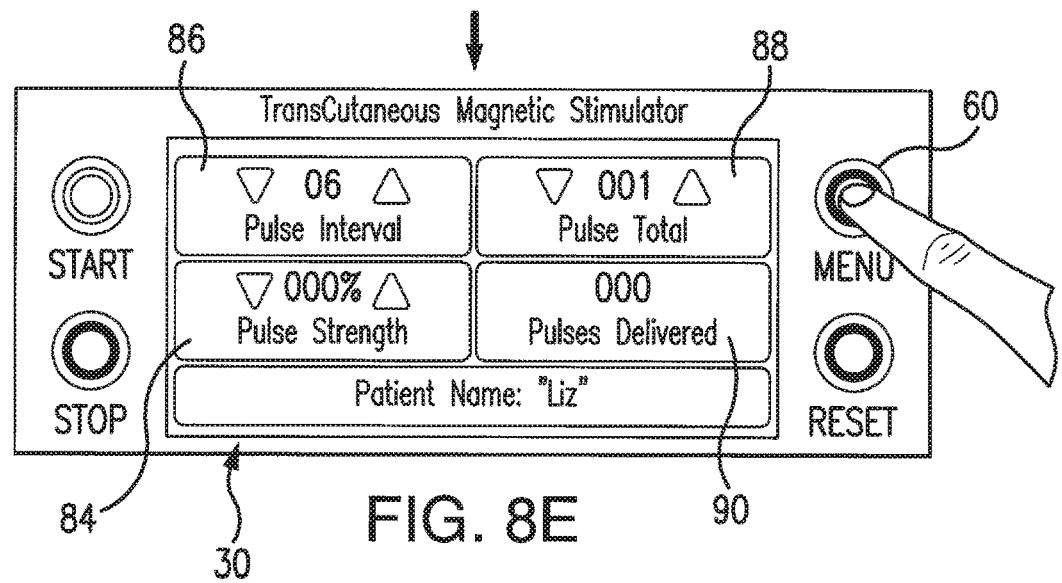
Figure 8F:
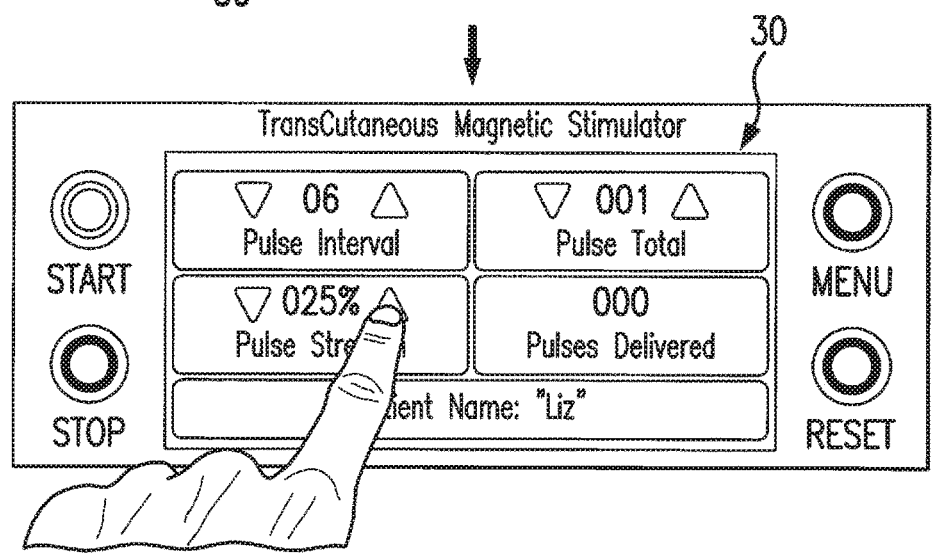

When the Menu feature has been selected, the screen shown in FIG. 8E is displayed, and the patient can adjust the settings as desired by touching the up or down arrows in the respective displays, as shown in FIG. 8F.

Figure 8G:
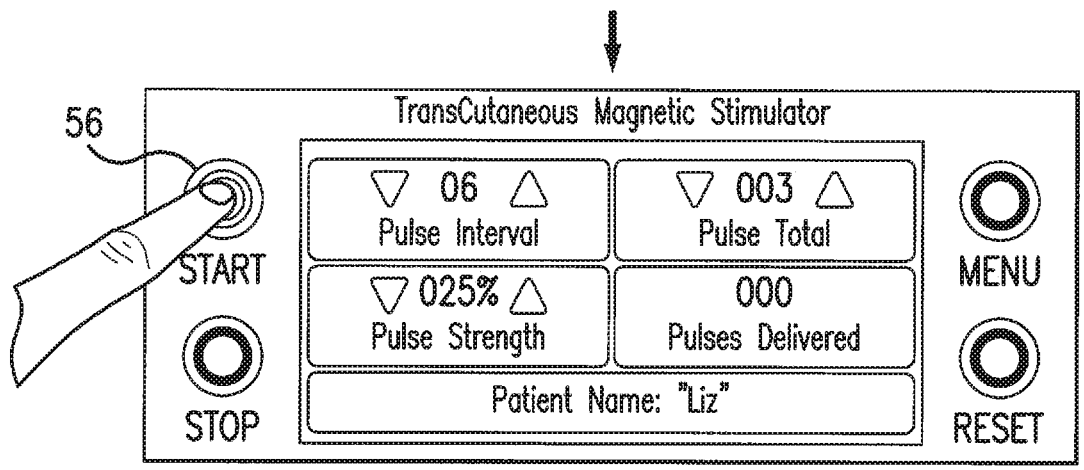

When the settings are successfully adjusted, the Start button 56 is pressed to begin treatment, as shown in FIG. 8G.

Figure 8H:
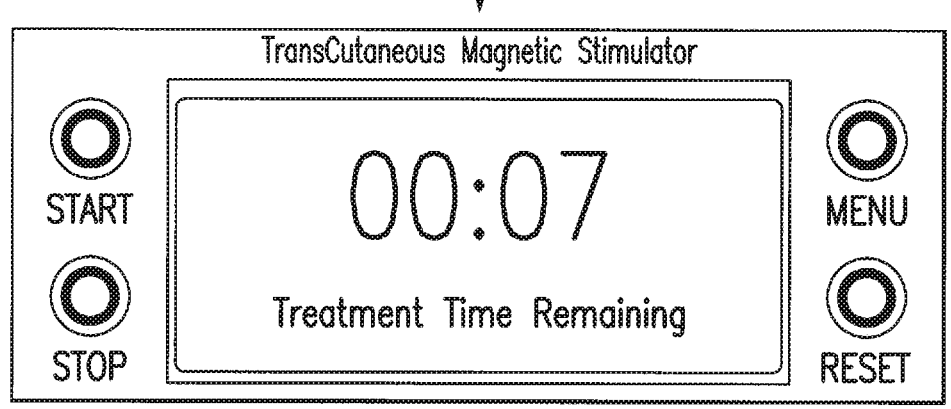

Once the treatment has started, the Start button 56 will illuminate and a countdown for the treatment is displayed in minutes and seconds, specifying the treatment time remaining as shown in FIG. 8H.

Figure 8I:
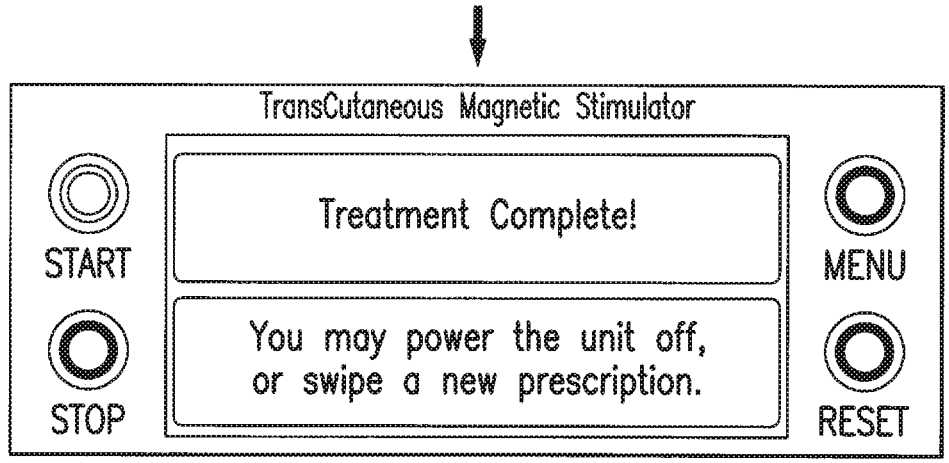

When the treatment is complete, the screen shown in FIG. 8I is displayed, and instructions to either power off the device, or swipe an RFID prescription card for another treatment are displayed.

Figure 8J:
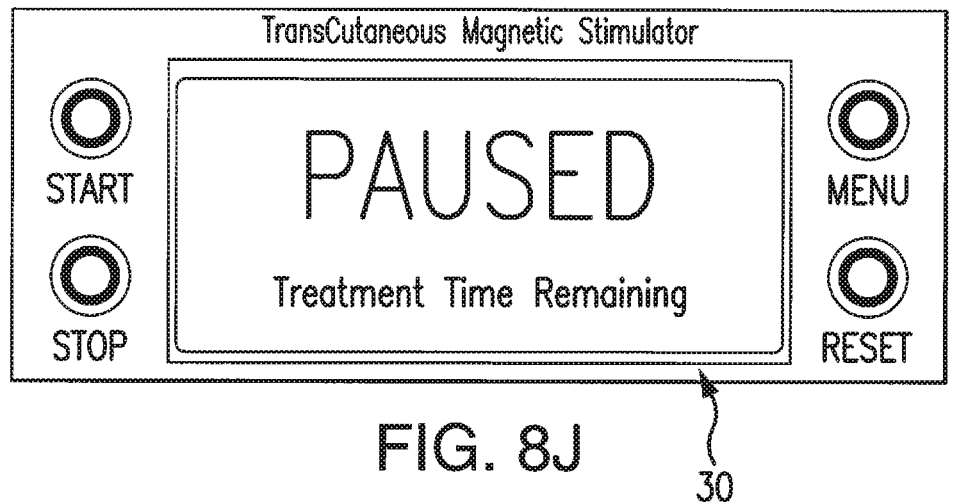

In the event that the treatment must be paused and further restarted where it is was interrupted, the following instructions are followed:

with the countdown screen active (shown in FIG. 8H), the Start button 56 is pressed. The treatment will continue for one pulse, and then pause, and the display 30 will show the identification "paused", as shown in FIG. 8J.

Following the paused display, the coil may be adjusted. When ready, the Start button 56 is pushed again to resume treatment.

Figure 8K:
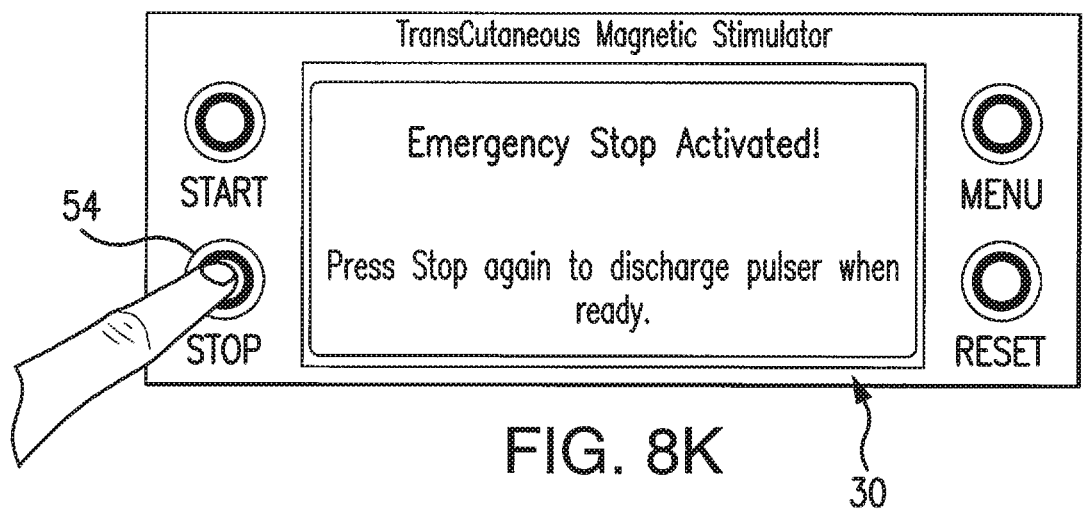

The subject system 10 includes an emergency stop feature. In the event that a treatment needs to be stopped unexpectedly, the following steps are followed:

With the countdown screen active (FIG. 8H), the Stop button 54 is pressed. Subsequently, the screen will display emergency stop actuated identification as shown in FIG. 8K. This situation may require the coil attachment to be adjusted, or the coil is to be moved to a safe place on a non-ferrous surface. In order to discharge the coil, the Stop button 54 is pressed as shown in the display 30.

Figure 9:
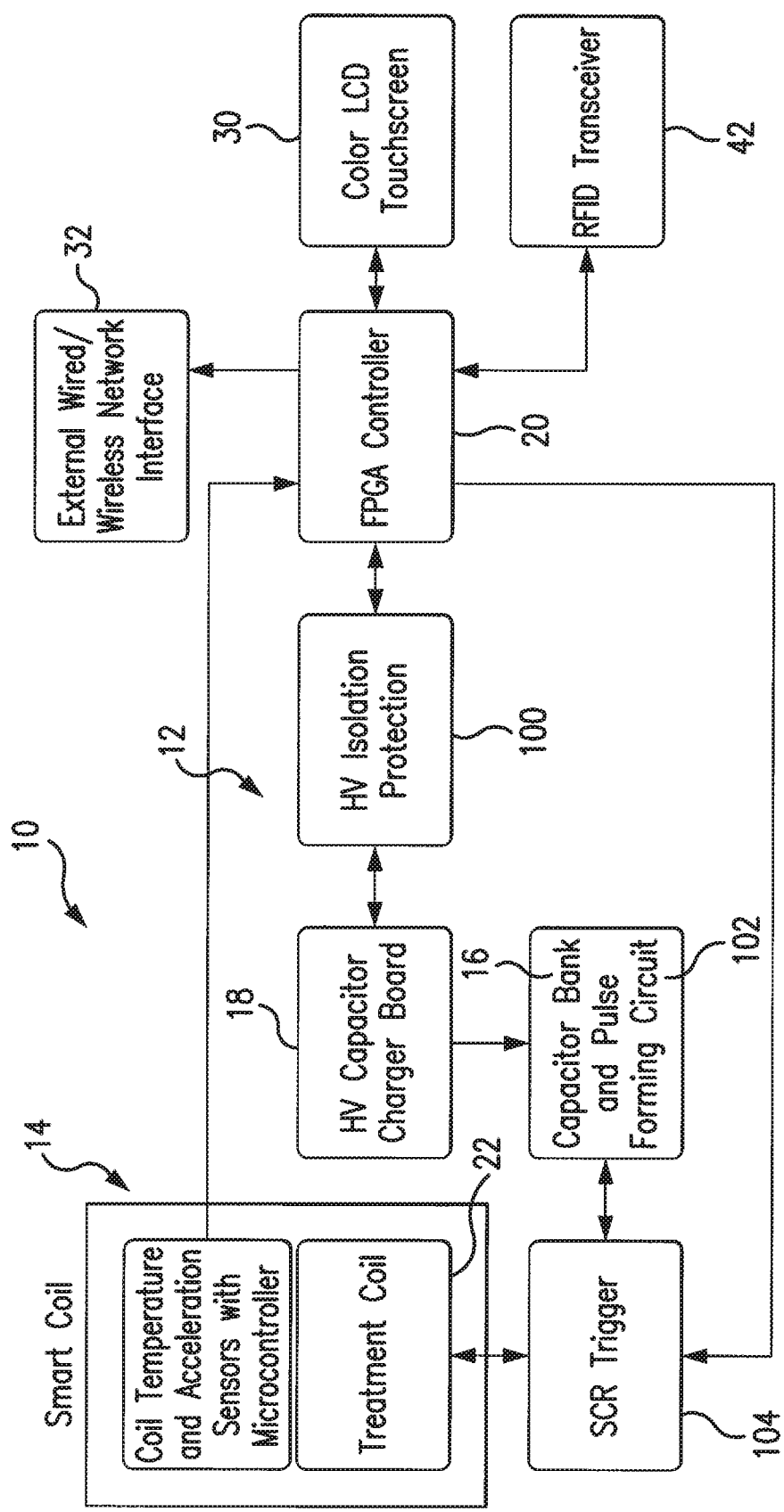
FIG. 9 is representative of a block diagram of the subject system.

Referring to FIG. 9, representative of a block diagram of the subject system 10, and returning to FIG. 1, the FPGA-based Pulser controller 20 operates with the RFID transceiver 42 to read the prescription, as well as the ID information on the pulse generator 12 and the coil attachment 14 to be used, provided in the E-script card 38.

In accordance with the information input from the E-script card 38 through the RFID transceiver 42, the FPGA controller 20, when the information is verified, controls the charger board (also referred to herein as capacitor charger control circuitry) 18 through the HV isolation protection circuit 100, the capacitor bank 16 and the pulse forming circuit 102 to activate or deactivate the Silicone Controlled Rectifier (SCR) trigger 104 to control the generation of magnetic fields at the treatment coil 22 embedded in the housing 24 of the coil attachment 14.

As presented in previous paragraphs in association with FIG. 1, the housing 24 of the coil attachment sub-system 14 includes coil temperature and acceleration sensors (and any other sensors needed for monitoring the operation of the device) 26, and the microcontroller 25.

The FPGA-based Pulser controller 20 (and specifically, the FPGA module 21 thereon) polls the coil temperature and acceleration sensors 26, and/or cooperates with the microcontroller 25 to acquire the temperature and acceleration (vibration) of the coil 22 within the housing 24 of the coil attachment sub-system 14.

The FPGA-based Pulser controller 20 subsequently transmits this information through the external wired/wireless network interface 32 to a central location 34 where the health of the system is remotely monitored, and diagnostics/statistical data are gathered. The information transmitted to the central facility is also used to detect fraud, schedule warranty service, and remotely control the pulse generation itself, if necessary.

The FPGA controller 20 bi-directionally communicates with the color LCD screen display 30 for the purposes presented in the previous paragraphs.

Figure 10:
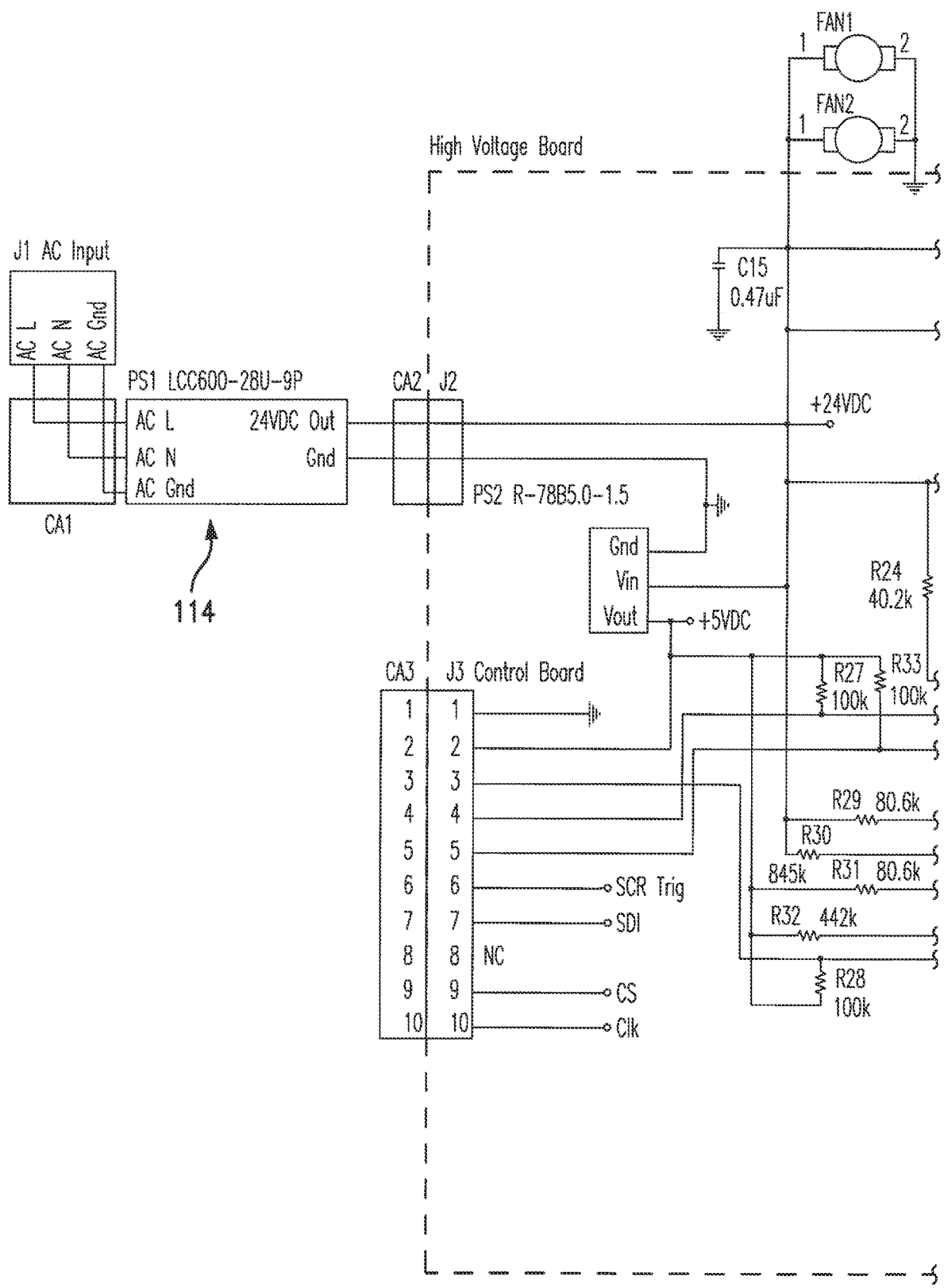
FIG. 10 is a schematic diagram of the high voltage (HV) control board and chassis embedded in the programmable pulse generator.
Figure 10:
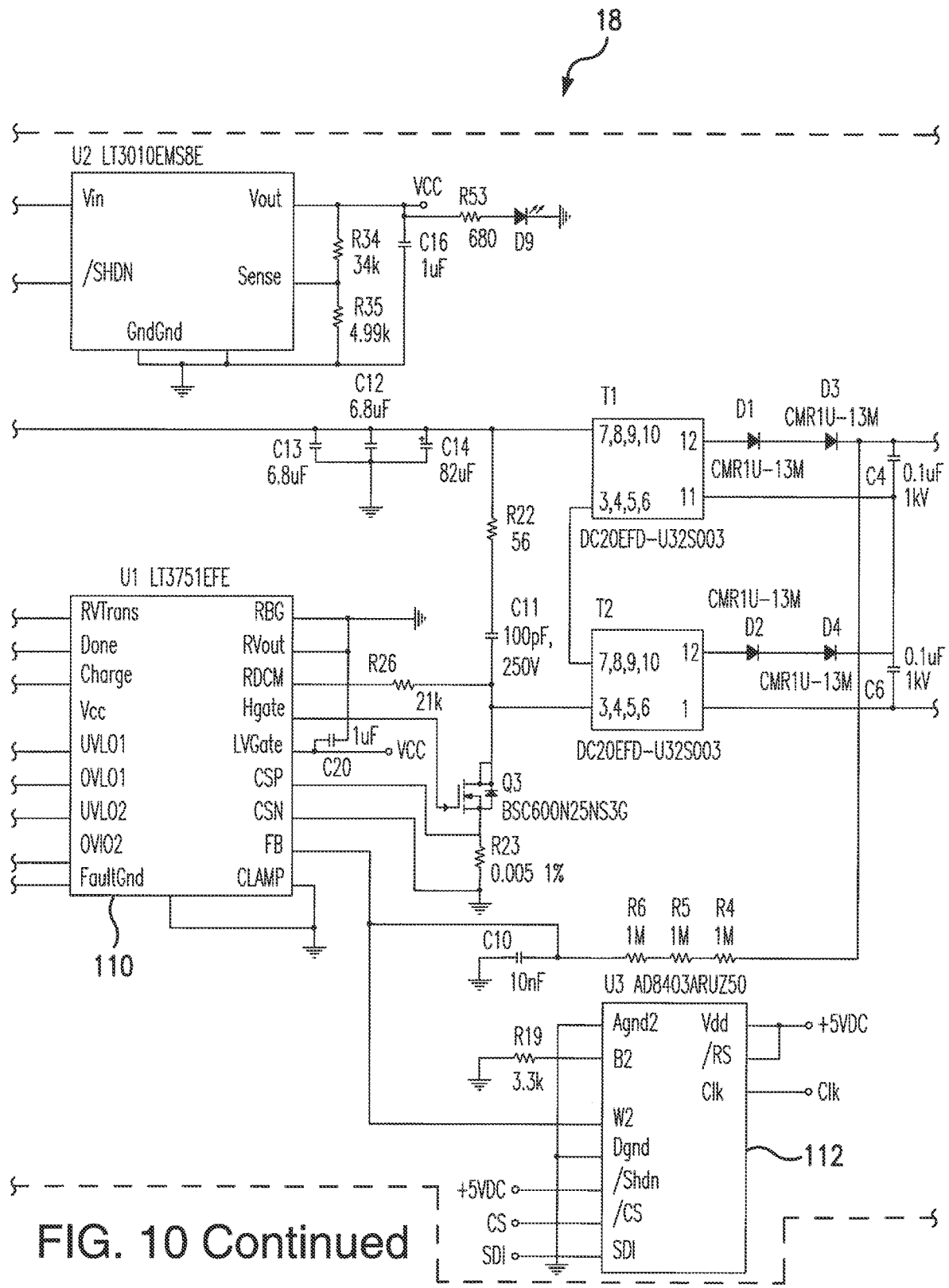
Figure 10:
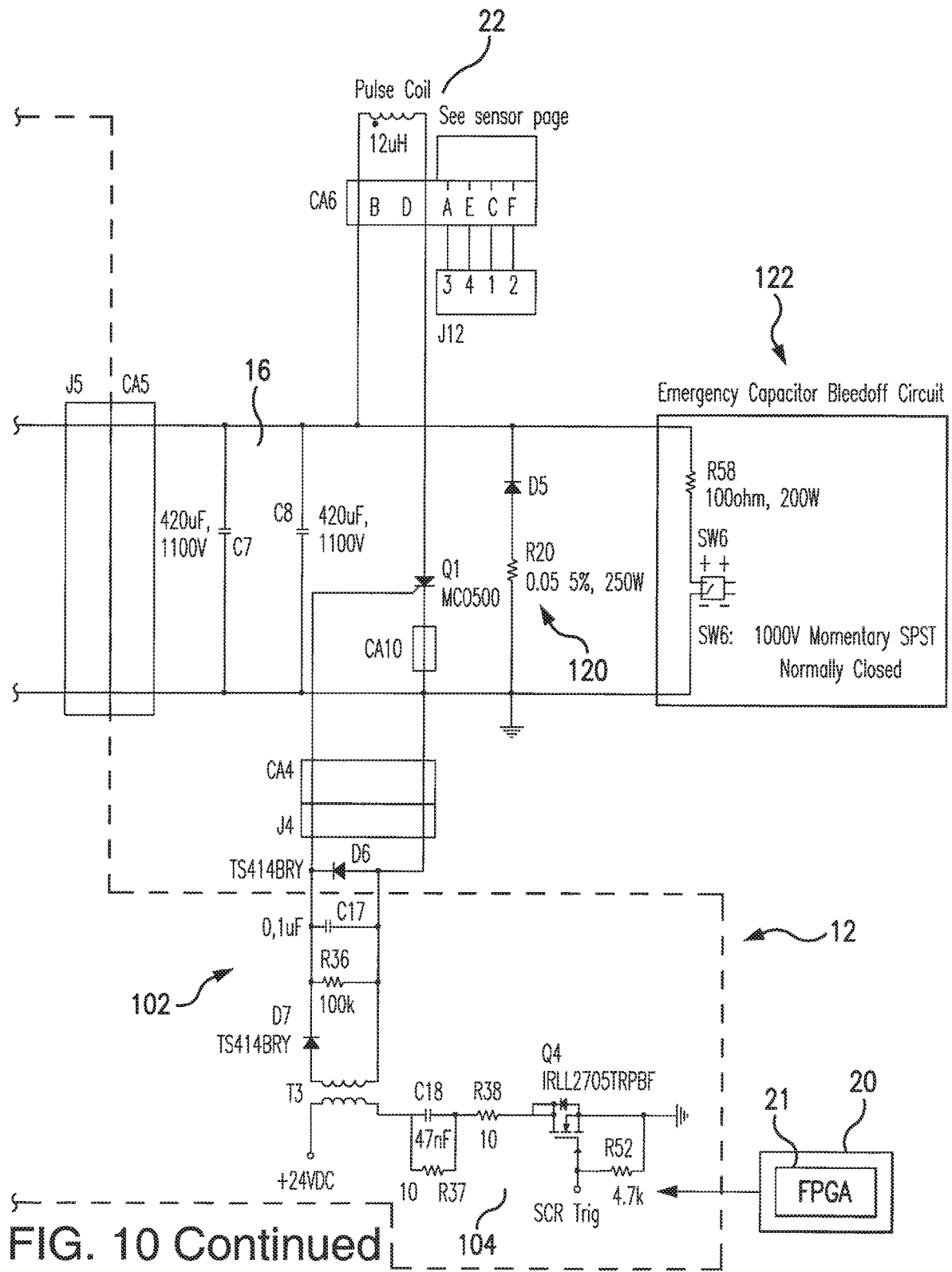

FIG. 10 is a schematic diagram of the high voltage (HV) board and chassis which includes the circuitry of the AC input path from a wall plug, the 24 VDC high current power supply, the HV capacitor charger board 18, the cooling fans, the treatment coil (coil attachment) and its connector/cable, the flyback circuit for the dampening current oscillations during the generation of the magnetic field pulse, and the emergency capacitor bleed-off circuit. Referring to FIG. 10, as well as to FIGS. 1 and 9, the high speed capacitor charger circuit 18 includes the LT3751 IC (shown in FIG. 10 as U1) whose support circuitry has been modified for the purposes of the subject system. The components in the schematic of the LT3751 IC which are based on the reference designs are not discussed herein. However, the unique modifications will be detailed in the following paragraphs.

Due to the requirement that the output power of the magnetic pulse be variable, the capacitor(s) 16 must be charged to different voltages. This is achieved by changing the feedback resistors on the FB pin 110 of the LT3751 IC (U1). Resistors R4-R6 and R19 are fixed, while the digital potentiometer 112 shown as U3 is controlled by the FPGA module 21 on the pulser control board 20 to adjust its resistance in a manner proportional to the user's input for the power level.

The input power for the HV charger 18 is generated by a 24 VDC 10A AC/DC converter (PS1) 114. This low voltage is stepped up to a higher voltage for the HV charging board 18.

Flyback transformers $T_1$ and $T_2$ are put in series to boost the maximum amount of voltage to the design specification of 1100 V.

Capacitors 16 (C7 and C8) are polymer film capacitors that store the large charge that is used to generate the magnetic pulse. They are discharged through the coil 22 (in the coil attachment) by activating the SCR Q1 which shorts one end of the coil to ground.

The driver circuit for the SCR (Silicon Controlled Rectifier) 104 is comprised of C17, C18, D6, D7, R36-R38, R52, Q4, and T3. T3 is a pulse transformer that builds up sufficient energy to generate a current pulse which in turn opens the conduction channel of the SCR Q4. This pulse is enabled by Q4 which is remotely triggered by the FPGA module 21 to generate the magnetic pulse in the coil 22.

A fly-back dampening circuit 120 includes the Diode D5 and Resistor R20. The requirement for the magnetic pulse is for a damped sine shape. Normally, the RLC circuit of the capacitors and coil (an inductor) will ring, something that was undesirable for both the desired output and the charging electronics, which would be damaged by the excess reflected energy. Thus, when the voltage of the capacitor(s) 16 goes negative during the discharge, the diode D5 turns ON and conducts the energy into the low resistance, i.e., high wattage resistor R20, where it is dissipated as heat.

Because large amounts of energy are stored in the capacitors C7 and C8, an additional protection circuit 122 is added for safety purposes in case the lid of the pulse generator's housing is opened when there is still charge remaining on the capacitors 16 (C7, C8). The protection circuit 122 includes the switch SW6 and resistor R58. When the case lid is open, switch SW6 closes, and shorts the capacitors C7, C8 through the resistor R58. This high wattage resistor R58 dissipates all the energy stored in the capacitors C7, C8.

Figure 11:
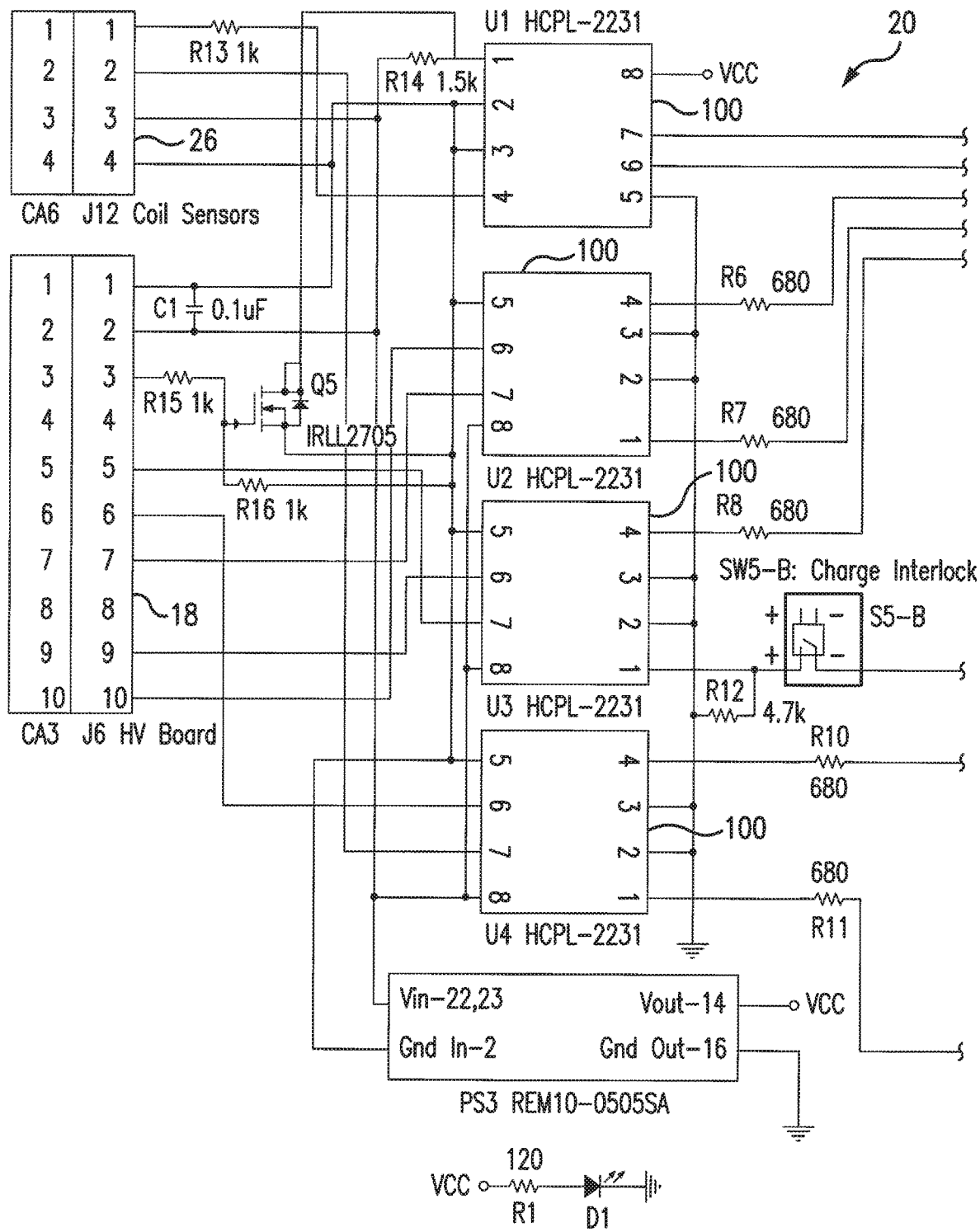
FIG. 11 is a schematic diagram of the pulser control board embedded in the programmable pulse generator.
Figure 11:
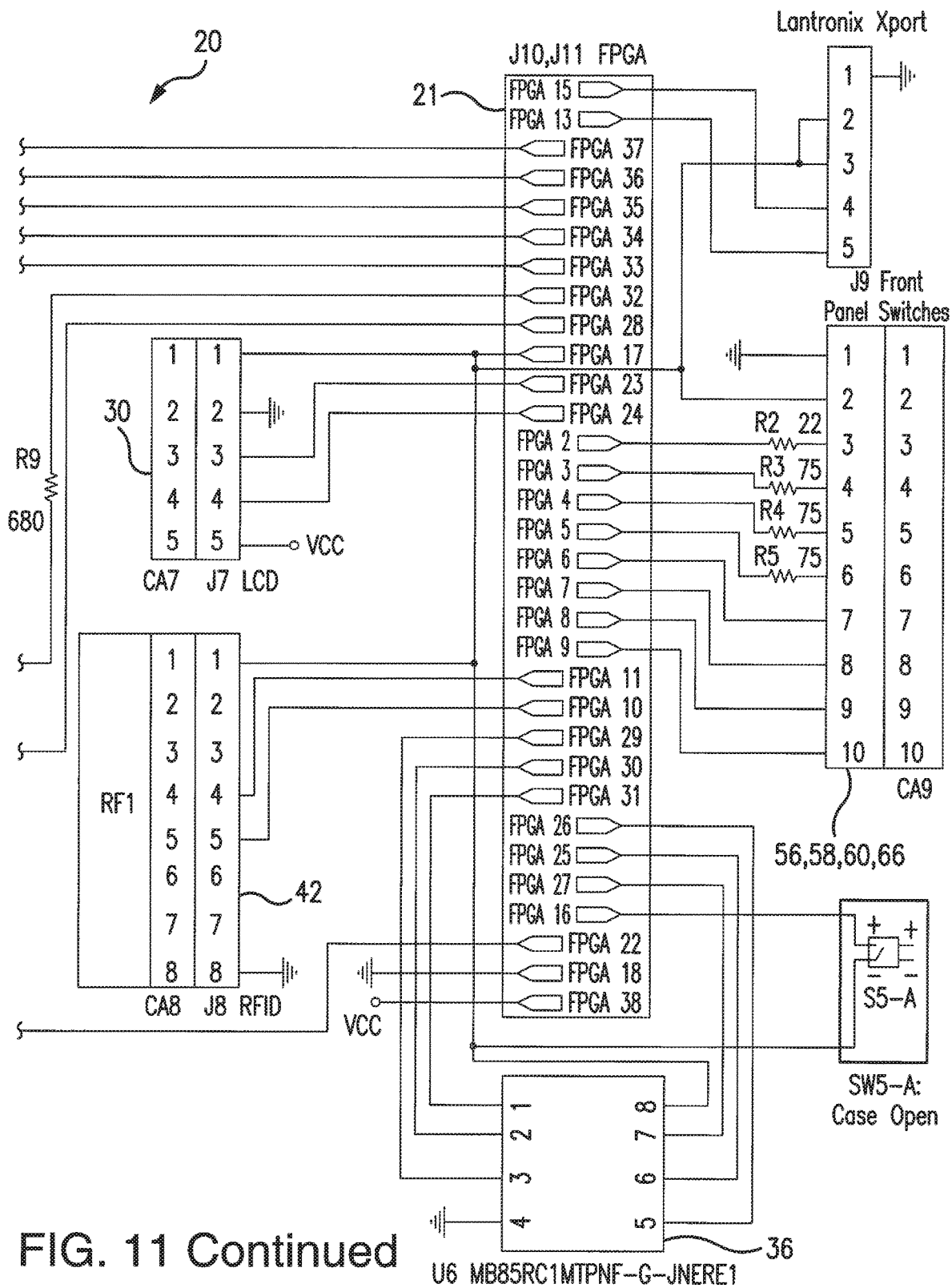

FIG. 11 is the schematics of the control board, also referred to herein as FPGA-based Pulser controller subsystem 20, which is responsible mainly for the following tasks, including:

1) processing user input from the front panel switches (buttons 54, 56, 60, 66) and the LCD screen 30, 2) isolating the controls on the front panel 50 (and by extension, the user) from the potential high voltage that could appear in the event of some kind of failure elsewhere in the device, 3) processing information received by the RFID card reader 42, and 4) sending signals to the HV board 18 to set the pulse generator's voltage set point, start a charge, stop a charge, and discharge the capacitors 16 through the coil 22.

The pulser control board 20 also includes the FPGA module 21 for the system control, the safety interlock switches the RFID module 42, the serial-Ethernet module 32, and the non-volatile flash memory storage 36.

The FPGA module 21 may be a commercially purchased module (Xess Corp. Xula2-LX25) that plugs into J10 and J11. Attached to it, is a non-volatile memory chip 36 (U6) that stores information after each pulse including the ID of the RFID card used to login, the pulse power, pulse interval, the coil's serial number, the pulse generator's serial number, and the total number of pulses generated by the pulse generator in its lifetime.

Due to the high voltages present inside the pulse generator 12 and the possibility of a conductive path from the HV (High Voltage) section to the LV (Low Voltage) control section, four optoisolators 100 (U1-U4), also referred to herein as HV isolation protection circuitry 100 (also shown in FIG. 9), are used to prevent any chance of high voltage from appearing on the parts of the system that the user could physically contact (for example, the front panel 50 components).

PS3 is an isolated DC/DC converter used also to prevent HV from appearing on the front panel 50 of the pulse generator housing 52.

SW5-A is one circuit of a DPST momentary switch mounted on the chassis that is depressed by the closing of the lid of the pulse generator's housing 52. When this switch SW5-A is closed, it lets the FPGA module 21 know that it is safe for the user to start the treatment.

If the case lid is open, the display 30 shows a "case open" warning and prevents any other input.

Switch SW5-B is part of the same switch, but instead physically breaks the "charge start" signal going to the HV board 18 that actually begins charging. This is an additional safety feature in case there is some failure of the FPGA that could send an inadvertent signal to the HV board.

R14-R16 and Q5 comprise a level shifting circuit for the fault signal coining from the capacitor charger chip 18.

The Lantronix Xport module is a serial-Ethernet converter that allows the pulse generator 12 to be remotely controlled. It can also output the same data found on the non-volatile memory chip 36, or stream live temperature data from the coil attachment. These features can be used for diagnostic purposes, for remote prescription verification, lockout, or remote diagnostics.

The RFID module 42 (J8) is a commercially available board using the PN532 chip configured to implement the NFC protocol. The RFID module 42 uses a serial command set for control by the FPGA module 21.

Figure 12:
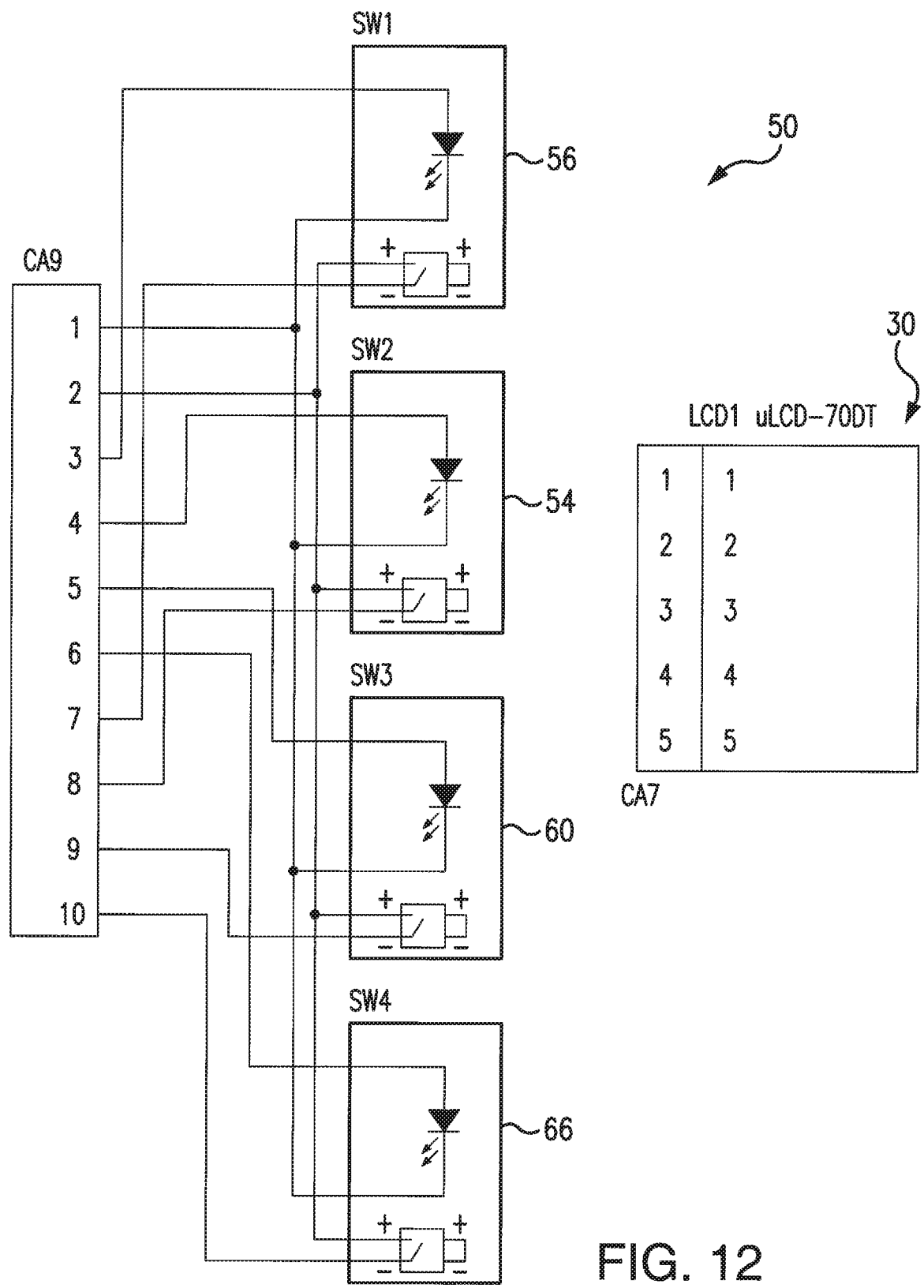
FIG. 12 is a schematic diagram of the front panel buttons and LCD touchscreen that enables the user control.

FIG. 12 depicts schematics of the circuitry underlying the operation of the front panel 50, four front panel buttons 54, 56, 60, 66, and the LCD touchscreen display 30 that enables the user control.

In FIG. 12, switches 54, 56, 60, and 66 may be momentary push-button switches that are used to gather user input commands for starting or pausing a treatment (SW1), stopping a treatment or discharging the capacitors (SW2), changing menu screens (SW3), or resetting treatment parameters (SW4). All switches have controllable illuminators, so the Start switch 56 is only lit during the treatment.

The LCD touchscreen 30 (LCD1) is a self-contained module that is used for the majority of user interfacing. It is controlled by the FPGA module 21 on the pulser control board 20 by a set of serial commands. The images displayed on the module are stored on a small SD card attached to the module.

FIG. 13 depicts a circuitry diagram of the coil attachment 14. This schematic shows the board which is installed in the housing 24 of the coil attachment 14 which is configured to sample thermocouples 26 mounted around the coil 22 to monitor temperature. The microcontroller 25 on the board also has the coil attachment's type and unique ID which are used by the pulse generator to validate the E-prescription. The temperature data is used to prevent the coil from overheating during usage.

Referring to FIG. 13, as well as FIGS. 1 and 9, the coil control board is centered on an Atmel ATMEGA328 microcontroller 25 (U5) that is running the open source Arduino software platform. U6 is the 3.3V power supply for the board. The microcontroller 25 reads data over an SPI interface from four MAX31855 thermocouple amplifier ICs 26 (U1-U4). Capacitors C7-C10 are used for noise reduction on the thermocouple signals.

Thermocouples 26 (1-4) are set strategically around the coil 22 to measure temperature changes in the winding over time. This information, in association with a unique serial number and the coil type ID, is transmitted over a TTL serial interface through the main cable to the pulse generator 12. This information is used to prevent the treatment from starting if the coil is too hot, stopping a treatment already underway if the coil becomes too hot, preventing a treatment from starting if the coil parameters do not match the prescription, and disabling all functions in the pulse generator if it cannot sense new data coining from the coil control board (for example, because the coil attachment is disconnected from the pulse generator).

Although this invention has been described in connection with specific forms and embodiments thereof, it will be appreciated that various modifications other than those discussed above may be resorted to without departing from the spirit or scope of the invention as defined in the appended claims. For example, functionally equivalent elements may be substituted for those specifically shown and described, certain features may be used independently of other features, and in certain cases, particular locations of elements, steps, or processes may be reversed or interposed, all without departing from the spirit or scope of the invention as defined in the appended claims.

What is claimed is:

1. A pain treatment system for controllable generation of magnetic pulses with electronic prescription verification, comprising:
    at least one intelligent coil attachment having a housing contoured in anatomical conformity to a patient's body part to be treated,
    said at least one coil attachment including:
        an electromagnetic coil,
        a sensor sub-system operatively coupled to said electromagnetic coil and having at least one sensor sensing at least one parameter corresponding to functionality of said electromagnetic coil, and
        a coil attachment control sub-system operatively coupled to said sensor sub-system, said coil attachment control sub-system being configured with a memory storage containing identification information of said coil attachment pre-programmed in said coil attachment,
    wherein said electromagnetic coil, said sensor sub-system, and said coil attachment control sub-system reside in said housing of said at least one intelligent coil attachment;
    a programmable pulse generator sub-system equipped with:
        at least one capacitor operatively coupled to said electromagnetic coil embedded in said at least one coil attachment,
        a capacitor charger circuitry operatively coupled to said at least one capacitor,
        a pulser control sub-system operatively coupled to said capacitor charger circuitry and said coil attachment control sub-system, and configured to control said capacitor charger circuitry to produce a controllable discharge protocol by said at least one capacitor, resulting in generation of controllably variable magnetic pulses by said electromagnetic coil residing in said at least one coil attachment, said pulser control sub-system including a memory storage containing identification information of said programmable pulse generator sub-system, and
        a RFID (Radio Frequency Identification) transceiver operatively coupled to said pulser control sub-system; and
    an electronic prescription card configured with memory storage containing a verification information including a treatment prescription protocol, a first serial number indicative of a programmable pulse generator to be used, and a second serial number indicative of a coil attachment to be used, wherein said RFID transceiver is configured to read said verification information contained in said memory storage of said electronic prescription card and transmit said verification information to said pulser control sub-system for storage in said memory storage of said pulser control sub-system;
    wherein said pulser control sub-system is further configured to execute a verification routine to find correspondence of said first serial number indicative of said programmable pulse generator to be used and said second serial number indicative of said coil attachment to be used to the identification information of said programmable pulse generator sub-system contained in said memory storage of said pulser control sub-system and said coil attachment's identification information received from said coil control sub-system, respectively, and to permit actuation of treatment in accordance to said treatment prescription protocol if said correspondence is found.

2. The system of claim 1, wherein said pulser control sub-system in said programmable pulse generator sub-system further includes a FPGA (Field-Programmable Logic Array) module residing in said pulser control sub-system, said FPGA module being configured to process said verification information obtained from said electronic prescription card, and, responsive to said processing of said verification information, to generate corresponding control signals supplied to said capacitor charger circuitry to adjust charging of said at least one capacitor to a charging voltage protocol corresponding to a required variable output power of magnetic pulses of interest in accordance with said treatment prescription protocol obtained from said electronic prescription card.

3. The system of claim 1, further including:
a system-user interface sub-system configured with a reconfigurable display operatively coupled to said pulser control sub-system and configured to display predetermined information under control of said pulser control sub-system.

4. The system of claim 3, wherein said display includes a color touchscreen and a system of functional buttons for a user to enter input commands, wherein said pulser control sub-system is further configured to process said input commands supplied thereto and to generate corresponding control signals for said capacitor charger circuitry to control the discharge protocol of said at least one capacitor.

5. The system of claim 4, wherein said capacitor charger circuitry is a high speed capacitor charger circuitry, further including a digital potentiometer controlled by said pulser control sub-system to adjust a resistance thereof in accordance to the user's input commands for a power level of the magnetic pulses.

6. The system of claim 1, wherein said at least one sensor in said sensor sub-system is selected from a group including a temperature sensor, an accelerometer sensor, and combination thereof, wherein said coil attachment control sub-system is configured to monitor readings of said at least one sensor and to transmit signals corresponding to said readings to said pulser control sub-system, and wherein said pulser control sub-system is further configured to monitor operational characteristics of said at least one coil attachment and to adjust operation of said capacitor charger circuitry responsive to said monitored operational characteristics of said at least one coil attachment to accommodate said treatment prescription protocol obtained from said electronic prescription card.

7. The system of claim 6, further including a network interface operatively coupled to said programmable pulse generator sub-system, wherein said pulser control sub-system is further configured to transmit said operational characteristics through said network interface to a remote facility to gather diagnostic information and remotely monitor operational health of said system.

8. The system of claim 7, wherein said treatment prescription protocol pre-programmed in said electronic prescription card is controllable remotely from a medical office through said network interface.

9. The system of claim 1, wherein said pulser control sub-system is configured to deny actuation of the treatment if said verification routine fails to find said correspondence between either of said first and second serial numbers to said identification information of said programmable pulse generator sub-system and said at least one coil attachment, respectively.

10. The system of claim 1, wherein said capacitor charger circuitry further includes a protection circuit operatively coupled to said at least one capacitor, said protection circuit includes a switch coupled in parallel to said at least one capacitor and a resistor coupled in series to said switch, said switch shorting said at least one capacitor through said resistor to dissipate energy of said at least one capacitor.

11. The system of claim 1, wherein said capacitor charger circuitry further includes a pulse transformer operatively coupled to said at least one capacitor, and a Silicon Controlled Rectifier (SCR) coupled to said pulse transformer, said pulse transformer operating to build up energy to generate a sufficient current pulse to open said SCR, wherein said SCR is remotely triggered by said pulser control sub-system to generate at least one of said controllably variable magnetic pulses in said at least one coil attachment.

12. A method for pain treatment by application of controllably generated magnetic pulses equipped with a routine for electronic prescription verification, comprising:
establishing at least one intelligent coil attachment having a housing contoured in anatomical conformity to a patient's body part to be treated,
disposing an electromagnetic coil in said housing,
operatively coupling a sensor sub-system to said electromagnetic coil in said housing, said sensor sub-system having at least one sensor sensing at least one parameter corresponding to functionality of said electromagnetic coil,
operatively coupling a coil control sub-system to said sensor sub-system in said housing,
configuring said coil control sub-system with a memory storage, and
storing identification information of said coil attachment in said memory storage of said coil control sub-system;
establishing a programmable pulse generator sub-system equipped with:
at least one capacitor operatively coupled to said coil embedded in said at least one coil attachment,
a capacitor charger circuitry operatively coupled to said at least one capacitor, and
a pulser control sub-system operatively coupled to said capacitor charger circuitry and said coil control sub-system,
configuring said pulser control sub-system to control an operation of said capacitor charger circuitry to produce a controllable discharge by said at least one capacitor to result in generation of controllably variable magnetic pulses by said electromagnetic coil,
forming said pulser control sub-system with memory storage containing identification information of said programmable pulse generator sub-system, and
an RFID transceiver operatively coupled to said pulser control sub-system;
configuring an electronic prescription card with a memory storage,
pre-programming said electronic prescription card with a verification information stored in said memory storage of said electronic prescription card, wherein said verification information includes:
a treatment prescription protocol, a first serial number indicative of a programmable pulse generator to be used, and a second serial number indicative of a coil attachment to be used;

reading said verification information by said RFID transceiver from said electronic prescription card and transmitting to said pulser control sub-system, storing said verification information in said memory storage of said pulser control sub-system, executing a verification routine by said pulser control sub-system to verify correspondence of said first and second serial numbers read by said RFID transceiver from said electronic prescription card to said programmable pulse generator sub-system's identification information and said coil attachment's identification information received from said coil control sub-system, respectively; and permitting actuation of a treatment protocol in correspondence to said treatment prescription protocol if said correspondence is found, and denying actuation of the treatment protocol if said verification fails.

13. The method of claim 12, further including the steps of:

coupling an FPGA module to said pulser control sub-system, configuring said FPGA module to process said verification information obtained from said electronic prescription card, and to generate corresponding control signals supplied to said capacitor charger circuitry, thereby adjusting charging of said at least one capacitor to a charging voltage protocol corresponding to a required variable output power of magnetic pulses of interest in accordance with said treatment prescription protocol.

14. The method of claim 13, further comprising the steps of:

forming said capacitor charger circuitry as a high speed capacitor charger circuitry, coupling a digital potentiometer to said high speed capacitor charger circuitry, controlling said digital potentiometer by said pulser control sub-system to adjust resistance of said digital potentiometer in accordance to input commands of the user for a power level of the magnetic pulses.

15. The method of claim 12, further including the steps of:

establishing a system-user interface sub-system configured with a reconfigurable display and user's commands entering mechanism, said user's commands entering mechanism having at least one indicia actuatable by the user to enter at least one command related to said treatment protocol, operatively coupling said reconfigurable display to said pulser control sub-system, and configuring said reconfigurable display to display various information to the user under control of said pulser control sub-system, processing, in said pulser control sub-system, said at least one command entered by the user through said user's commands entering mechanism, and generating, by said pulser control sub-system, corresponding control signals supplied to said capacitor charger circuitry for controlling a discharge protocol of said at least one capacitor.

16. The method of claim 12, wherein said at least one sensor in said sensor sub-system is selected from a group including a temperature sensor, an accelerometer sensor, and combination thereof, further comprising the steps of:

monitoring, by said coil control sub-system, readings of said at least one sensor, transmitting, by said coil control sub-system, said readings to said pulser control sub-system to monitor said at least one coil attachment operational characteristics, and adjusting, by said pulser control sub-system, the operation of said capacitor charger circuitry in accordance with said monitored operational characteristics of said at least one coil attachment to accommodate said treatment prescription protocol obtained from said electronic prescription card.

17. The method of claim 16, further comprising the steps of:

operatively coupling a network interface to said programmable pulse generator sub-system, transmitting said operational characteristics through said network interface to a remote facility to gather diagnostic information and remotely monitor operational health of said system.

18. The method of claim 17, further comprising the step of:

verifying said treatment prescription protocol in said electronic prescription card remotely from a medical office through said network interface.

19. The method of claim 12, further comprising the steps of:

operatively coupling a protection circuit to said at least one capacitor, configuring said protection circuit with a switch in series with a resistor coupled in parallel to said at least one capacitor, wherein said switch shorts said at least one capacitor through said resistor to dissipate energy of said at least one capacitor.

20. The method of claim 12, further comprising the steps of:

operatively coupling a pulse transformer to said at least one capacitor, coupling a Silicon Controlled Rectifier (SCR) to said pulse transformer, operating said pulse transformer to build up energy to generate a sufficient current pulse to open said SCR, and remotely triggering said SCR by said pulser control sub-system to generate at least one magnetic pulse of said controllably variable magnetic pulses in said at least one coil attachment.

\* \* \* \* \*